(12) United States Patent
Medoff et al.

(10) Patent No.: US 9,963,727 B2
(45) Date of Patent: May 8, 2018

(54) PRODUCTION OF PRODUCTS FROM BIOMASS

(71) Applicant: Xyleco, Inc., Woburn, MA (US)

(72) Inventors: Marshall Medoff, Brookline, MA (US); Thomas Craig Masterman, Brookline, MA (US); Jaewoong Moon, Andover, MA (US); Aiichiro Yoshida, Canton, MA (US)

(73) Assignee: XYLECO, INC., Wakefield, MA (US)

( * ) Notice: Subject to any disclaimer, the term of this patent is extended or adjusted under 35 U.S.C. 154(b) by 0 days. days.

(21) Appl. No.: 14/016,481

(22) Filed: Sep. 3, 2013

(65) Prior Publication Data

US 2014/0004574 A1    Jan. 2, 2014

Related U.S. Application Data

(63) Continuation of application No. PCT/US2012/071083, filed on Dec. 20, 2012.

(60) Provisional application No. 61/579,576, filed on Dec. 22, 2011.

(51) Int. Cl.
| | |
|---|---|
| *C12P 19/14* | (2006.01) |
| *C12P 7/18* | (2006.01) |
| *C12P 7/20* | (2006.01) |
| *C12P 19/02* | (2006.01) |

(52) U.S. Cl.
CPC ............... *C12P 19/14* (2013.01); *C12P 7/18* (2013.01); *C12P 7/20* (2013.01); *C12P 19/02* (2013.01)

(58) Field of Classification Search
CPC  C12P 19/02; C12P 19/14; C12P 19/12; C12P 19/04; C12P 7/20
USPC .......................... 435/99, 100, 101, 105, 159
See application file for complete search history.

(56) References Cited

U.S. PATENT DOCUMENTS

| | | | |
|---|---|---|---|
| 4,939,091 A | 7/1990 | Sasaki | |
| 5,036,011 A | 7/1991 | Sasaki | |
| 5,902,739 A | 5/1999 | Abe et al. | |
| 5,962,287 A | 10/1999 | Suh | |
| 5,981,241 A | 11/1999 | Cho | |
| 5,989,878 A | 11/1999 | Kim | |
| 6,060,291 A | 5/2000 | Park | |
| 6,074,857 A | 6/2000 | Chida | |
| 6,110,715 A | 8/2000 | Chida et al. | |
| 6,270,815 B1 | 8/2001 | Kim et al. | |
| 6,365,383 B1 | 4/2002 | Segueilha | |
| 6,448,053 B1 | 9/2002 | Lin | |
| 6,455,301 B1 | 9/2002 | Lin et al. | |
| 6,916,639 B2 | 7/2005 | Lin | |
| 8,187,847 B2 | 5/2012 | Edlauer et al. | |
| 2001/0008769 A1 | 7/2001 | Cho et al. | |
| 2001/0055796 A1 | 12/2001 | Seo | |
| 2002/0132313 A1 | 9/2002 | Lin et al. | |
| 2003/0235881 A1 | 12/2003 | Heikkila et al. | |
| 2007/0037266 A1 | 2/2007 | Sasman | |
| 2009/0246843 A1 | 10/2009 | Edlauer et al. | |
| 2010/0200806 A1 | 8/2010 | Medoff et al. | |
| 2010/0297705 A1* | 11/2010 | Medoff et al. | 435/72 |

FOREIGN PATENT DOCUMENTS

| | | |
|---|---|---|
| CN | 101849018 A | 9/2010 |
| CN | 102066063 A | 5/2011 |
| EP | 0136802 | 4/1987 |
| EP | 0845538 A2 * | 3/1998 |
| EP | 0940471 | 9/1999 |
| EP | 1088893 | 4/2001 |
| EP | 1092781 | 4/2001 |
| JP | H05503844 | 6/1993 |
| JP | 09-154589 | 7/1997 |
| JP | 2009148211 | 7/2009 |
| JP | 2010104361 | 5/2010 |
| KR | 10-2002-0035051 | 5/2002 |
| WO | 2008040036 A2 | 4/2008 |
| WO | WO 2009026707 A1 * | 3/2009 |
| WO | 2009045651 | 4/2009 |
| WO | 2009134748 | 11/2009 |
| WO | 2010135365 | 11/2010 |

OTHER PUBLICATIONS

Wisniak J et al. Hydrogenation of Xylose to Xylitol. 1972. Industrial & Engineering Chemistry Product Research and Development. Vo. 13, No. 1. p. 75-79.*
Skoog K et al. Effect of Oxygenation on Xylose Fermentation by Pichia stipitis. 1990. Applied and Environmental Microbiology. 56(11):3389-3394.*
Lee J et al. Increased erythritol production in *Torula* sp. with inositol and phytic acid. 2001. Biotechnology Letters. 23:497-500.*
Baucher et al. (2003) "Lignin:Genetic Engineering and Impact on Pulping," Crit. Rev. Biochem. Mol. Biol. 38:305-350.
Chen et al. (2007) "Lignin Modification Improves Fermentable Sugar Yields for Biofuel Production," Nat. Biotechnol. 25:759-61.
Kumar et al (2009) "Methods for Pretreatment of Lignocellulosic Biomass for Efficient Hydrolysis and Biofuel Production," Ind. Eng. Chem. Res. 48:3713-29.
Moon, H-J, et al., "Biotechnological production of erythritol and its applications," Appl. Microbiol. Biotechnol., vol. 86: 1017-1025 (2010).
Dooms, L. et al., "Polyol synthesis and taxonomic characters in the genus," Antonie van Leeuwenhoek, vol. 37: 107-118 (1971).
Ryu, Y-W, et al., "Optimization of erythritol production by Candida magnoliae in fed-batch culture," J. Ind. Microbiol. Biotechnol., vol. 25: 100-103 (2000).
International Search Report issued for PCT/US2012/071083, dated Mar. 12, 2013 (3 pages).
Singapore Search Report, Corresponding Singapore Application No. 11201402958W, dated Feb. 11, 2015, 11 pages.

(Continued)

*Primary Examiner* — Paul J Holland
(74) *Attorney, Agent, or Firm* — Leber IP Law; Shelly M. Fujikawa

(57) ABSTRACT

The processes disclosed herein include saccharifying cellulosic and/or lignocellulosic biomass and fermenting the sugars to produce a sugar alcohol.

24 Claims, 6 Drawing Sheets

(56) References Cited

OTHER PUBLICATIONS

China Office Action—Corresponding Chinese Application No. 201280062596.7, dated Dec. 2, 2015, 7 pages.

Martinez, A.T. et al., "Physiological Characteristics of Moniliella, Trichosporonoides and Hyalodendron", Studies in Mycology, No. 19, Dec. 29, 1979, pp. 58-68.

Jeya, M. et al., "Isolation of a Novel High Erythritol-Producing Pseudozyma Tsukubaenis and Scale-Up of Erythritol Fermentation to Industrial Level", Appl. Microbiol. Biotechnol. vol. 83, 2009, pp. 225-231.

Rymowicz, W. et al., "High-Yield Production of Erythritol from Raw Glycerol in Fed-Batch Cultures of Yarrowia Lipolytica", Biotechnol. Lett., vol. 31, 2009, pp. 377-380.

Aoki, M. et al., "Microbial Transformation of Sucrose and Glucose to Erythritol", Biotechnology Letters, vol. 15, No. 4, Apr. 1993, pp. 383-388.

Moon, H.J. et al., "Biotechnological Production of Erythritol and its Applications", Appl. Microbiol. Biotechnol., vol. 86, 2010, pp. 1017-1025.

Savergave, Laxman, "Microbial Production of Erythritol and Mannitol: Strain Improvement and Process Optimization", Thesis submitted to the University of Pune, Aug. 2011, 283 pages.

Office Action—Corresponding Egyptian Application No. 20140601005, dated Mar. 9, 2016, 4 pages.

Search Report—Corresponding Chinese Application No. 2012800625967, dated Jul. 13, 2016, 2 pages.

Bergeron, P.W. et al., "Wastepaper as a Feedstock for Ethanol Production", National Renewable Energy Laboratory, Nov. 1991, 29 pages.

Lin et al., 'High-Level Production of Erythritol by Mutants of Osmophilic *Moniliella* sp.;' Process Biochemistry 45; 2010; pp. 973-979.

Office Action cited in corresponding JP Application No. 2014-548918 dated May 9, 2017 (6 pages).

Office Action dated Jun. 14, 2017, issued by the Ukrainian Patent Office in related UA Patent Application 201408101 (11 pages).

Pretrial Report—Corresponding Japanese Application No. 2014-548918, dated Nov. 14, 2017, 3 pages.

\* cited by examiner (Prior Art Apparatus)

(Prior Art Apparatus)

(Prior Art Apparatus)

(Prior Art Apparatus)

(Prior Art Apparatus)

(Prior Art Apparatus)

PRODUCTION OF PRODUCTS FROM BIOMASS

CROSS REFERENCE TO RELATED APPLICATION

This application is a continuation of PCT/US2012/071083 filed Dec. 20, 2012, which claimed priority to U.S. Provisional Application No. 61/579,576, filed on Dec. 22, 2011. The entirety of the disclosure in the above applications is incorporated herein by reference.

FIELD OF THE INVENTION

The invention pertains to the production of products, e.g., sugar alcohols, e.g., such as erythritol.

BACKGROUND

As demand for petroleum increases, so too does interest in renewable feedstocks for manufacturing biofuels and biochemicals. The use of lignocellulosic biomass as a feedstock for such manufacturing processes has been studied since the 1970s. Lignocellulosic biomass is attractive because it is abundant, renewable, domestically produced, and does not compete with food industry uses.

Many potential lignocellulosic feedstocks are available today, including agricultural residues, woody biomass, municipal waste, oilseeds/cakes and sea weeds, to name a few. At present these materials are either used as animal feed, biocompost materials, are burned in a cogeneration facility or are landfilled.

Lignocellulosic biomass is recalcitrant to degradation as the plant cell walls have a structure that is rigid and compact. The structure comprises crystalline cellulose fibrils embedded in a hemicellulose matrix, surrounded by lignin. This compact matrix is difficult to access by enzymes and other chemical, biochemical and biological processes. Cellulosic biomass materials (e.g., biomass material from which substantially all the lignin has been removed) can be more accessible to enzymes and other conversion processes, but even so, naturally-occurring cellulosic materials often have low yields (relative to theoretical yields) when contacted with hydrolyzing enzymes. Lignocellulosic biomass is even more recalcitrant to enzyme attack. Furthermore, each type of lignocellulosic biomass has its own specific composition of cellulose, hemicellulose and lignin.

While a number of methods have been tried to extract structural carbohydrates from lignocellulosic biomass, they are either too expensive, produce too low a yield, leave undesirable chemicals in the resulting product, or simply degrade the sugars.

Saccharides from renewable biomass sources could become the basis of the chemical and fuels industries by replacing, supplementing or substituting petroleum and other fossil feedstocks. However, techniques need to be developed that will make these monosaccharides available in large quantities and at acceptable purities and prices.

SUMMARY OF THE INVENTION

A method is provided for making a sugar alcohol from a cellulosic or lignocellulosic biomass that contains one or more sugars that includes combining the cellulosic or lignocellulosic biomass with a microorganism that is capable of converting at least one of the sugars to a sugar alcohol, and maintaining the microorganism-biomass combination under conditions that enable the microorganism to convert at least one of the sugars to the sugar alcohol. In some implementations, the method includes: providing a cellulosic or lignocellulosic biomass, wherein the cellulosic or lignocellulosic biomass contains one or more sugars; providing a microorganism that is capable of converting at least one of the sugars to a sugar alcohol; combining the cellulosic or lignocellulosic biomass with the microorganism, thereby producing a microorganism-biomass combination; and maintaining the microorganism-biomass combination under conditions that enable the microorganism to convert at least one of the sugars to a sugar alcohol; thereby making a sugar alcohol from a cellulosic or lignocellulosic biomass. The cellulosic or lignocellulosic biomass can be saccharified.

Any of the methods provided herein can include reducing the recalcitrance of the cellulosic or lignocellulosic biomass to saccharification prior to combining it with the microorganism. The recalcitrance can be reduced by a treatment method selected from the group consisting of: bombardment with electrons, sonication, oxidation, pyrolysis, steam explosion, chemical treatment, mechanical treatment, and freeze grinding. The treatment method can be bombardment with electrons.

Any of the methods provided herein can also include mechanically treating the cellulosic or lignocellulosic biomass to reduce its bulk density and/or increase its surface area. For instance, the cellulosic or lignocellulosic biomass can be comminuted, for instance, it can be dry milled, or it can be wet milled.

In any of the methods provided herein, the biomass can be saccharified with one or more cellulases. Any of the methods can also include separating one or more sugars prior to combining the cellulosic or lignocellulosic biomass with the microorganism, or the methods can include concentrating the one or more sugars prior to combining the cellulosic or lignocellulosic biomass with the microorganism. The methods can also include both concentrating and separating one or more sugars prior to combining the cellulosic or lignocellulosic biomass with the microorganism. The saccharified biomass can be adjusted to have an initial glucose concentration of at least 5 wt %. The saccharified biomass can also be purified, for instance, by the removal of metal ions.

Any of the methods disclosed herein can also include culturing the microorganism in a cell growth phase before combining the cellulosic or lignocellulosic biomass with the microorganism.

In any of the methods provided herein, the sugar alcohol can be glycol, glycerol, erythritol, threitol, arabitol, xylitol, ribitol, mannitol, sorbitol, galactitol, iditol, inositol, volemitol, isomalt, maltitol, lactitol, maltotriitol, maltotetraitol, or polyglycitol.

The microorganism can be *Moniliella pollinis, Moniliella megachiliensis, Yarrowia lipolytica, Aureobasidium* sp., *Trichosporonoides* sp., *Trigonopsis variabilis, Trichosporon* sp., *Moniliellaacetoabutans, Typhula variabilis, Candida magnoliae, Ustilaginomycetes, Pseudozyma tsukubaensis*; yeast species of genera *Zygosaccharomyces, Debaryomyces, Hansenula* and *Pichia*, or fungi of the dematioid genus *Torula*. The microorganism can be a species of *Moniliella*, such as *M. pollinis*, for instance, strain CBS 461.67, or *M. megachiliensis*, strain CBS 567.85.

In any of the methods provided herein, the cellulosic or lignocellulosic biomass can be: paper, paper products, paper waste, paper pulp, pigmented papers, loaded papers, coated papers, filled papers, magazines, printed matter, printer paper, polycoated paper, card stock, cardboard, paperboard, cotton, wood, particle board, forestry wastes, sawdust, aspen wood, wood chips, grasses, switchgrass, miscanthus, cord grass, reed canary grass, grain residues, rice hulls, oat hulls, wheat chaff, barley hulls, agricultural waste, silage, canola straw, wheat straw, barley straw, oat straw, rice straw, jute, hemp, flax, bamboo, sisal, abaca, corn cobs, corn stover, soybean stover, corn fiber, alfalfa, hay, coconut hair, sugar processing residues, bagasse, beet pulp, agave bagasse, algae, seaweed, manure, sewage, offal, arracacha, buckwheat, banana, barley, cassava, kudzu, oca, sago, sorghum, potato, sweet potato, taro, yams, beans, favas, lentils, peas, or mixtures of any of these.

It should be understood that this invention is not limited to the embodiments disclosed in this Summary, and it is intended to cover modifications that are within the spirit and scope of the invention, as defined by the claims.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION

This invention relates to methods of processing biomass feedstock materials (e.g., biomass materials or biomass-derived materials such as cellulosic and lignocellulosic materials) to obtain sugar alcohols such as erythritol ((2R, 3S)-butane-1,2,3,4-tetraol), or isomers, or mixtures thereof.

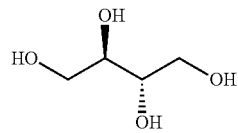

In some instances, the recalcitrance of the feedstock is reduced prior to saccharification. In some cases, reducing the recalcitrance of the feedstock includes treating the feedstock. The treatment can, for example, be radiation, e.g., electron beam radiation, sonication, pyrolysis, oxidation, steam explosion, chemical treatment, or combinations of any of these.

In some implementations, the method also includes mechanically treating the feedstock before and/or after reducing its recalcitrance. Mechanical treatments include, for example, cutting, milling, e.g., hammermilling, pressing, grinding, shearing and chopping. Mechanical treatment may reduce the bulk density of the feedstock and/or increase the surface area of the feedstock. In some embodiments, after mechanical treatment the material has a bulk density of less than 0.75 g/cm3, e.g., less than about 0.7, 0.65, 0.60, 0.50, 0.35, 0.25, 0.20, 0.15, 0.10, 0.05, or less, e.g., less than 0.025 g/cm3. Bulk density is determined using ASTM D1895B. Under some circumstances, mechanical treatments can remove or reduce recalcitrance.

In one aspect, the invention features a method that includes contacting a sugar, produced by saccharifying a cellulosic or lignocellulosic feedstock with a microorganism to produce a product, such as a sugar alcohol e.g., erythritol. Other products include, for example, citric acid, lysine and glutamic acid.

In some implementations, the microorganism includes *Moniliella pollinis, Yarrowia lipolytica, Aureobasidium* sp., *Trichosporonoides* sp., *Trigonopsis variabilis, Trichosporon* sp., *Moniliellaacetoabutans, Typhula variabilis, Candida magnoliae, Ustilaginomycetes, Pseudozyma tsukubaensis*; yeast species of genera *Zygosaccharomyces, Debaryomyces, Hansenula* and *Pichia*; and fungi of the dematioid genus *Torula*.

In some implementations, the contacting step includes a dual stage process, comprising a cell growth step and a fermentation step. Optionally, the fermentation is performed using a glucose solution having an initial glucose concentration of at least 5 wt. % at the start of the fermentation. Furthermore, the glucose solution can be diluted after fermentation has begun.

Figure 1:
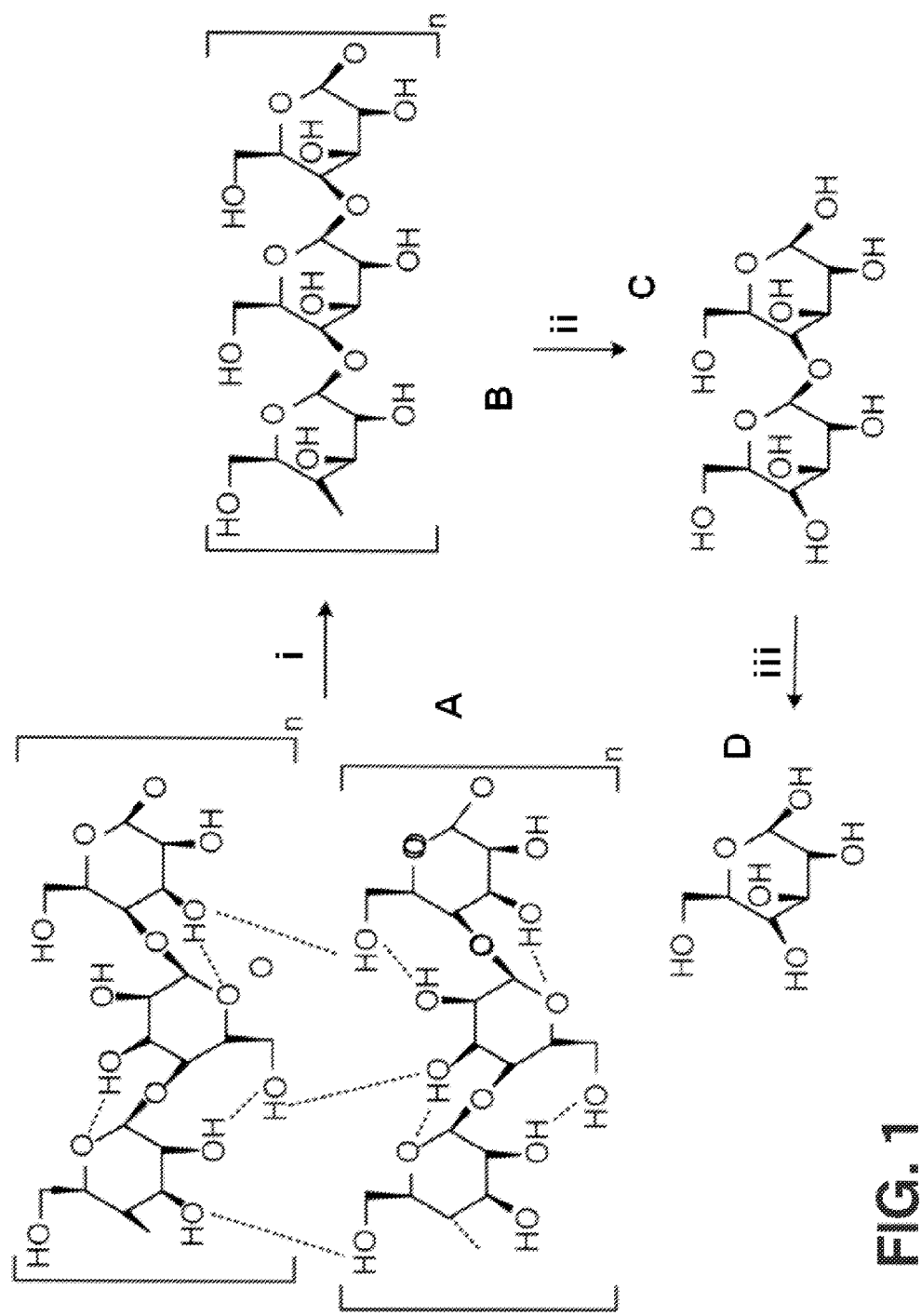
FIG. 1 is a diagram illustrating the enzymatic hydrolysis of cellulose to glucose. Cellulosic substrate (A) is converted by endocellulase (i) to cellulose (B), which is converted by exocellulase (ii) to cellobiose (C), which is converted to glucose (D) by cellobiase (beta-glucosidase) (iii).

As shown in FIG. 1, for example, during saccharification a cellulosic substrate (A) is initially hydrolyzed by endoglucanases (i) at random locations producing oligomeric intermediates (e.g., cellulose) (B). These intermediates are then substrates for exo-splitting glucanases (ii) such as cellobiohydrolase to produce cellobiose from the ends of the cellulose polymer. Cellobiose is a water-soluble 1,4-linked dimer of glucose. Finally cellobiase (iii) cleaves cellobiose (C) to yield glucose (D). Therefore, the endoglucanases are particularly effective in attacking the crystalline portions of cellulose and increasing the effectiveness of exocellulases to produce cellobiose, which then requires the specificity of the cellobiose to produce glucose. Therefore, it is evident that depending on the nature and structure of the cellulosic substrate, the amount and type of the three different enzymes may need to be modified.

In some implementations, the enzyme is produced by a fungus, e.g., by strains of the cellulolytic filamentous fungus

*Trichoderma reesei*. For example, high-yielding cellulase mutants of *Trichoderma reesei* may be used, e.g., RUT-NG14, PC3-7, QM9414 and/or Rut-C30. Such strains are described, for example, in "Selective Screening Methods for the Isolation of High Yielding Cellulase Mutants of *Trichoderma reesei*," Montenecourt, B. S. and Everleigh, D. E., *Adv. Chem. Ser.* 181, 289-301 (1979), the full disclosure of which is incorporated herein by reference. Other cellulase-producing microorganisms may also be used.

Figure 2:
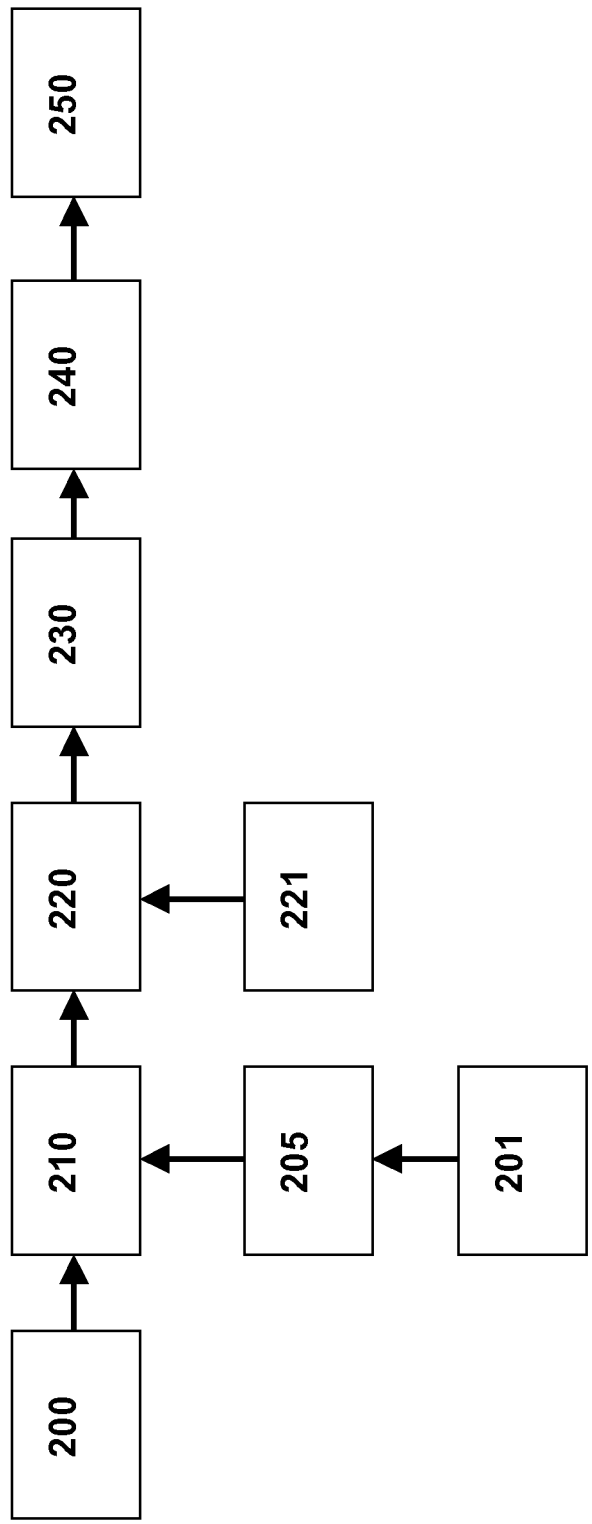
FIG. 2 is a flow diagram illustrating conversion of a biomass feedstock to one or more products. Feedstock is physically pretreated (e.g., to reduce its size) (200), optionally treated to reduce its recalcitrance (210), saccharified to form a sugar solution (220), the solution is transported (230) to a manufacturing plant (e.g., by pipeline, railcar) (or if saccharification is performed en route, the feedstock, enzyme and water is transported), the saccharified feedstock is bio-processed to produce a desired product (e.g., alcohol) (240), and the product can be processed further, e.g., by distillation, to produce a final product (250). Treatment for recalcitrance can be modified by measuring lignin content (201) and setting or adjusting process parameters (205). Saccharifying the feedstock (220) can be modified by mixing the feedstock with medium and the enzyme (221).

As shown in FIG. 2, a process for manufacturing a sugar alcohol can include, for example, optionally mechanically treating a feedstock, e.g., to reduce its size (200), before and/or after this treatment, optionally treating the feedstock with another physical treatment to further reduce its recalcitrance (210), then saccharifying the feedstock, using the enzyme complex, to form a sugar solution (220). Optionally, the method may also include transporting, e.g., by pipeline, railcar, truck or barge, the solution (or the feedstock, enzyme and water, if saccharification is performed en route) to a manufacturing plant (230). In some cases the saccharified feedstock is further bioprocessed (e.g., fermented) to produce a desired product e.g., alcohol (240). This resulting product may in some implementations be processed further, e.g., by distillation (250), to produce a final product. One method of reducing the recalcitrance of the feedstock is by electron bombardment of the feedstock. If desired, the steps of measuring lignin content of the feedstock (201) and setting or adjusting process parameters based on this measurement (205) can be performed at various stages of the process, as described in U.S. Pat. App. Pub. 2010/0203495 A1 by Medoff and Masterman, published Aug. 12, 2010, the complete disclosure of which is incorporated herein by reference. Saccharifying the feedstock (220) can also be modified by mixing the feedstock with medium and the enzyme (221).

In some cases, the feedstock is boiled, steeped, or cooked in hot water prior to saccharification, as described in U.S. Ser. No. 13/276,192, filed Oct. 18, 2011.

The processes described above can be partially or completely performed in a tank (e.g., a tank having a volume of at least 4000, 40,000, or 500,000 L) in a manufacturing plant, and/or can be partially or completely performed in transit, e.g., in a rail car, tanker truck, or in a supertanker or the hold of a ship. Mobile fermenters can be utilized, as described in U.S. Pat. App. Pub. 2010/0064746 A1, published on Mar. 18, 2010, the entire disclosure of which is incorporated by reference herein.

It is generally preferred that the tank and/or fermenter contents be mixed during all or part of the process, e.g., using jet mixing as described in U.S. Pat. App. Pub. 2010/0297705 A1, filed May 18, 2010 and published on Nov. 25, 2012, U.S. Pat. App. Pub. 2012/0100572 A1, filed Nov. 10, 2011 and published on Apr. 26, 2012, U.S. Pat. App. Pub. 2012/0091035 A1, filed Nov. 10, 2011 and published on Apr. 19, 2012, the full disclosures of which are incorporated by reference herein.

The addition of additives such as e.g., surfactants or nutrients, can enhance the rate of saccharification. Examples of surfactants include non-ionic surfactants, such as a Tween® 20 or Tween® 80 polyethylene glycol surfactants, ionic surfactants, or amphoteric surfactants.

One or more useful products may be produced. For example glycol, glycerol, erythritol, threitol, arabitol, xylitol, ribitol, mannitol, sorbitol, galactitol, iditol, inositol, volemitol, isomalt, maltitol, lactitol, maltotriitol, maltotetraitol, and polyglycitol can be produced by fermentation. In addition, butyric acid, gluconic acid and citric acid also can be produced.

In some embodiments, polyols can be made by fermentation, including monomeric polyols such as glycerin, pentaerythritol, ethylene glycol, and sucrose. These can be built up into polymeric polyols such as polyether polyols.

In some embodiments, the optionally mechanically and/or physically treated feedstock can be combined with an enzyme complex for saccharification and is also combined with an organism that ferments at least a part of the released sugars to a sugar alcohol. The sugar alcohol is then isolated from other products and non-fermented material such as solids, un-fermentable sugars and cellular debris.

The optionally mechanically and/or physically treated feedstock can also be combined with an enzyme complex for saccharification and after the saccharification is at least partially completed, the mixture is combined with an organism that produces sugar alcohols. The conditions for saccharification (e.g., temperature, agitation, aeration) can be different than the conditions for fermentation. The optimum pH for fermentation is generally from about pH 4 to 6. Typical fermentation times are about 24 to 120 hours with temperatures in the range of 25° C. to 40° C., e.g., 25° C. to 30° C. Fermentation is typically done with aeration using a sparging tube and an air and/or oxygen supply to maintain the dissolved oxygen level above about 10% (e.g., above about 20%). The saccharification and fermentation can be in the same or different reactor/vessel. The sugar alcohol is then isolated. As discussed above, the fermentation can be performed during a transportation process.

Generally, a high initial sugar concentration at the start of fermentation favors the production of sugar alcohols. Accordingly, the saccharified feedstock solution can be concentrated prior to combination with the organism that produces sugar alcohols to increase the glucose level of the solution. Concentration can be done by any desired technique. For example, concentration can be by heating, cooling, centrifugation, reverse osmosis, chromatography, precipitation, crystallization, evaporation, adsorption and combinations thereof. Preferably concentration is done by evaporation of at least a portion of the liquids from the saccharified feedstock. Concentration is preferably done to increase the glucose content to greater than about 5 wt %, e.g., greater than 10 wt. %, greater than 15 wt. %, greater than 20 wt. %, greater than 30 wt. %, greater than 40 wt. % or even greater than 50 wt. %. The product from the fermentation is then isolated.

The saccharified feedstock can also be purified before or after concentration. Purification is preferably done to increase the glucose content to greater than about 50 wt. % of all components other than water (e.g., greater than about 60 wt. %, greater than about 70 wt. %, greater than about 80 wt. %, greater than about 90 wt. % and even greater than about 99 wt. %). Purification can be done by any desired technique, for example, by heating, cooling, centrifugation, reverse osmosis, chromatography, precipitation, crystallization, evaporation, adsorption or combinations of any of these.

In some implementations the fermentation is dual-stage, with a cell growth phase and a product production phase. In the growth phase, conditions are selected to optimize cell growth, while in the production phase conditions are selected to optimize production of the desired fermentation products. Generally, low sugar levels (e.g., between 0.1 and 10 wt. %, between 0.2 and 5 wt. %) in the growth medium favor cell growth, and high sugar levels (e.g., greater than 5 wt. %, greater than about 10 wt. %, greater than 20 wt. %, greater than 30 wt. %, greater than 40 wt. %) in the fermentation medium favor product production. Other conditions can be optionally modified in each stage, for example, temperature, agitation, sugar levels, nutrients and/or pH. Monitoring of conditions in each stage can be done to optimize the process. For example, growth can be monitored to achieve an optimum density, e.g., about 50 g/L (e.g., greater than 60 g/L, greater than 70 g/L or greater than about 75 g/L), and a concentrated saccharified solution can be added to trigger the onset of product formation. Optionally, the process can be optimized, for example, by monitoring and adjusting the pH or oxygenation level with probes and automatic feeding to control cell growth and product formation. Furthermore, other nutrients can be controlled and monitored to optimize the process (e.g., amino acids, vitamins, metal ions, yeast extract, vegetable extracts, peptones, carbon sources and proteins).

Dual-stage fermentations are described in *Biotechnological production of erythritol and its applications*, Hee-Jung Moon et al., *Appl. Microbiol. Biotechnol.* (2010) 86:1017-1025. While generally a high initial concentration of glucose at the start of the fermentation favors erythritol production, if this high concentration is maintained too long it may be detrimental to the organism. A high initial glucose concentration can be achieved by concentrating glucose during or after saccharification as discussed above. After an initial fermentation time to allow the start of fermentation, the fermentation media is diluted with a suitable diluent so that the glucose level is brought below about 60 wt. % (e.g., below about 50 wt. %, below about 40 wt. %). The diluent can be water or water with additional components such as amino acids, vitamins, metal ions, yeast extract, vegetable extracts, peptones, carbon sources and proteins.

Biomass Materials

As used herein, the term "biomass materials" includes lignocellulosic, cellulosic, starchy, and microbial materials.

Lignocellulosic materials include, but are not limited to, wood, particle board, forestry wastes (e.g., sawdust, aspen wood, wood chips), grasses, (e.g., switchgrass, miscanthus, cord grass, reed canary grass), grain residues, (e.g., rice hulls, oat hulls, wheat chaff, barley hulls), agricultural waste (e.g., silage, canola straw, wheat straw, barley straw, oat straw, rice straw, jute, hemp, flax, bamboo, sisal, abaca, corn cobs, corn stover, soybean stover, corn fiber, alfalfa, hay, coconut hair), sugar processing residues (e.g., bagasse, beet pulp, agave bagasse), algae, seaweed, manure, sewage, and mixtures of any of these.

In some cases, the lignocellulosic material includes corncobs. Ground or hammermilled corncobs can be spread in a layer of relatively uniform thickness for irradiation, and after irradiation are easy to disperse in the medium for further processing. To facilitate harvest and collection, in some cases the entire corn plant is used, including the corn stalk, corn kernels, and in some cases even the root system of the plant.

Advantageously, no additional nutrients (other than a nitrogen source, e.g., urea or ammonia) are required during fermentation of corncobs or cellulosic or lignocellulosic materials containing significant amounts of corncobs.

Corncobs, before and after comminution, are also easier to convey and disperse, and have a lesser tendency to form explosive mixtures in air than other cellulosic or lignocellulosic materials such as hay and grasses.

Cellulosic materials include, for example, paper, paper products, paper waste, paper pulp, pigmented papers, loaded papers, coated papers, filled papers, magazines, printed matter (e.g., books, catalogs, manuals, labels, calendars, greeting cards, brochures, prospectuses), newsprint, printer paper, polycoated paper, card stock, cardboard, paperboard, materials having a high α-cellulose content such as cotton, and mixtures of any of these. For example paper products as described in U.S. application Ser. No. 13/396,365 filed Feb. 14, 2012 (publication No. 2013-0052687-A1, published Feb. 28, 2013), the full disclosure of which is incorporated herein by reference.

Cellulosic materials can also include lignocellulosic materials which have been de-lignified.

Starchy materials include starch itself, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, oca, sago, sorghum, regular household potatoes, sweet potato, taro, yams, or one or more beans, such as favas, lentils or peas. Blends of any two or more starchy materials are also starchy materials. Mixtures of starchy, cellulosic and or lignocellulosic materials can also be used. For example, a biomass can be an entire plant, a part of a plant or different parts of a plant, e.g., a wheat plant, cotton plant, a corn plant, rice plant or a tree. The starchy materials can be treated by any of the methods described herein.

Microbial materials include, but are not limited to, any naturally occurring or genetically modified microorganism or organism that contains or is capable of providing a source of carbohydrates (e.g., cellulose), for example, protists, e.g., animal protists (e.g., protozoa such as flagellates, amoeboids, ciliates, and sporozoa) and plant protists (e.g., algae such alveolates, chlorarachniophytes, cryptomonads, euglenids, glaucophytes, haptophytes, red algae, stramenopiles, and viridaeplantae). Other examples include seaweed, plankton (e.g., macroplankton, mesoplankton, microplankton, nanoplankton, picoplankton, and femptoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture and fermentation systems.

The biomass material can also include offal, and similar sources of material.

In other embodiments, the biomass materials, such as cellulosic, starchy and lignocellulosic feedstock materials, can be obtained from transgenic microorganisms and plants that have been modified with respect to a wild type variety. Such modifications may be, for example, through the iterative steps of selection and breeding to obtain desired traits in a plant. Furthermore, the plants can have had genetic material removed, modified, silenced and/or added with respect to the wild type variety. For example, genetically modified plants can be produced by recombinant DNA methods, where genetic modifications include introducing or modifying specific genes from parental varieties, or, for example, by using transgenic breeding wherein a specific gene or genes are introduced to a plant from a different species of plant and/or bacteria. Another way to create genetic variation is through mutation breeding wherein new alleles are artificially created from endogenous genes. The artificial genes can be created by a variety of ways including treating the plant or seeds with, for example, chemical mutagens (e.g., using alkylating agents, epoxides, alkaloids, peroxides, formaldehyde), irradiation (e.g., X-rays, gamma rays, neutrons, beta particles, alpha particles, protons, deuterons, UV radiation) and temperature shocking or other external stressing and subsequent selection techniques. Other methods of providing modified genes is through error prone PCR and DNA shuffling followed by insertion of the desired modified DNA into the desired plant or seed. Methods of introducing the desired genetic variation in the seed or plant include, for example, the use of a bacterial carrier, biolistics, calcium phosphate precipitation, electroporation, gene splicing, gene silencing, lipofection, microinjection and viral carriers. Additional genetically modified materials have been described in U.S. application Ser. No. 13/396,369 filed Feb. 14, 2012 (Publication No. 2013-0052682 published Feb. 28, 2013) the full disclosure of which is incorporated herein by reference.

Any of the methods described herein can be practiced with mixtures of any biomass materials described herein.

Biomass Material Preparation—Mechanical Treatments

The biomass can be in a dry form, for example with less than about 35% moisture content (e.g., less than about 20%, less than about 15%, less than about 10% less than about 5%, less than about 4%, less than about 3%, less than about 2% or even less than about 1%). The biomass can also be delivered in a wet state, for example as a wet solid, a slurry or a suspension with at least about 10 wt % solids (e.g., at least about 20 wt. %, at least about 30 wt. %, at least about 40 wt. %, at least about 50 wt. %, at least about 60 wt. %, at least about 70 wt. %).

The processes disclosed herein can utilize low bulk density materials, for example cellulosic or lignocellulosic feedstocks that have been physically pretreated to have a bulk density of less than about 0.75 g/cm$^3$, e.g., less than about 0.7, 0.65, 0.60, 0.50, 0.35, 0.25, 0.20, 0.15, 0.10, 0.05 or less, e.g., less than about 0.025 g/cm$^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters. If desired, low bulk density materials can be densified, for example, by methods described in U.S. Pat. No. 7,971,809 to Medoff, the full disclosure of which is hereby incorporated by reference.

In some cases, the pre-treatment processing includes screening of the biomass material. Screening can be through a mesh or perforated plate with a desired opening size, for example, less than about 6.35 mm (¼ inch, 0.25 inch), (e.g., less than about 3.18 mm (⅛ inch, 0.125 inch), less than about 1.59 mm (1/16 inch, 0.0625 inch), is less than about 0.79 mm (1/32 inch, 0.03125 inch), e.g., less than about 0.51 mm (1/50 inch, 0.02000 inch), less than about 0.40 mm (1/64 inch, 0.015625 inch), less than about 0.23 mm (0.009 inch), less than about 0.20 mm (1/128 inch, 0.0078125 inch), less than about 0.18 mm (0.007 inch), less than about 0.13 mm (0.005 inch), or even less than about 0.10 mm (1/256 inch, 0.00390625 inch)). In one configuration the desired biomass falls through the perforations or screen and thus biomass larger than the perforations or screen are not irradiated. These larger materials can be re-processed, for example by comminuting, or they can simply be removed from processing. In another configuration material that is larger than the perforations is irradiated and the smaller material is removed by the screening process or recycled. In this kind of a configuration, the conveyor itself (for example a part of the conveyor) can be perforated or made with a mesh. For example, in one particular embodiment the biomass material may be wet and the perforations or mesh allow water to drain away from the biomass before irradiation.

Screening of material can also be by a manual method, for example by an operator or mechanoid (e.g., a robot equipped with a color, reflectivity or other sensor) that removes unwanted material. Screening can also be by magnetic screening wherein a magnet is disposed near the conveyed material and the magnetic material is removed magnetically.

Optional pre-treatment processing can include heating the material. For example a portion of the conveyor can be sent through a heated zone. The heated zone can be created, for example, by IR radiation, microwaves, combustion (e.g., gas, coal, oil, biomass), resistive heating and/or inductive coils. The heat can be applied from at least one side or more than one side, can be continuous or periodic and can be for only a portion of the material or all the material. For example, a portion of the conveying trough can be heated by use of a heating jacket. Heating can be, for example, for the purpose of drying the material. In the case of drying the material, this can also be facilitated, with or without heating, by the movement of a gas (e.g., air, oxygen, nitrogen, He, $CO_2$, Argon) over and/or through the biomass as it is being conveyed.

Optionally, pre-treatment processing can include cooling the material. Cooling material is described in U.S. Pat. No. 7,900,857 to Medoff, the disclosure of which in incorporated herein by reference. For example, cooling can be by supplying a cooling fluid, for example water (e.g., with glycerol), or nitrogen (e.g., liquid nitrogen) to the bottom of the conveying trough. Alternatively, a cooling gas, for example, chilled nitrogen can be blown over the biomass materials or under the conveying system.

Another optional pre-treatment processing method can include adding a material to the biomass. The additional material can be added by, for example, by showering, sprinkling and or pouring the material onto the biomass as it is conveyed. Materials that can be added include, for example, metals, ceramics and/or ions as described in U.S. Pat. App. Pub. 2010/0105119 A1 published Apr. 29, 2010 (filed Oct. 26, 2009) and U.S. Pat. App. Pub. 2010/0159569 A1 published Jun. 24, 2010 (filed Dec. 16, 2009), the entire disclosures of which are incorporated herein by reference. Optional materials that can be added include acids and bases. Other materials that can be added are oxidants (e.g., peroxides, chlorates), polymers, polymerizable monomers (e.g., containing unsaturated bonds), water, catalysts, enzymes and/or organisms. Materials can be added, for example, in pure form, as a solution in a solvent (e.g., water or an organic solvent) and/or as a solution. In some cases the solvent is volatile and can be made to evaporate e.g., by heating and/or blowing gas as previously described. The added material may form a uniform coating on the biomass or be a homogeneous mixture of different components (e.g., biomass and additional material). The added material can modulate the subsequent irradiation step by increasing the efficiency of the irradiation, damping the irradiation or changing the effect of the irradiation (e.g., from electron beams to X-rays or heat). The method may have no impact on the irradiation but may be useful for further downstream processing. The added material may help in conveying the material, for example, by lowering dust levels.

Biomass can be delivered to the conveyor by a belt conveyor, a pneumatic conveyor, a screw conveyor, a hopper, a pipe, manually or by a combination of these. The biomass can, for example, be dropped, poured and/or placed onto the conveyor by any of these methods. In some embodiments the material is delivered to the conveyor using an enclosed material distribution system to help maintain a low oxygen atmosphere and/or control dust and fines. Lofted or air suspended biomass fines and dust are undesirable because these can form an explosion hazard or damage the window foils of an electron gun (if such a device is used for treating the material).

The material can be leveled to form a uniform thickness between about 0.0312 and 5 inches (e.g., between about 0.0625 and 2.000 inches, between about 0.125 and 1 inches, between about 0.125 and 0.5 inches, between about 0.3 and 0.9 inches, between about 0.2 and 0.5 inches between about 0.25 and 1.0 inches, between about 0.25 and 0.5 inches, 0.100+/−0.025 inches, 0.150+/−0.025 inches, 0.200+/−0.025 inches, 0.250+/−0.025 inches, 0.300+/−0.025 inches, 0.350+/−0.025 inches, 0.400+/−0.025 inches, 0.450+/−0.025 inches, 0.500+/−0.025 inches, 0.550+/−0.025 inches, 0.600+/−0.025 inches, 0.700+/−0.025 inches, 0.750+/−0.025 inches, 0.800+/−0.025 inches, 0.850+/−0.025 inches, 0.900+/−0.025 inches, 0.900+/−0.025 inches.

Generally, it is preferred to convey the material as quickly as possible through the electron beam to maximize throughput. For example the material can be conveyed at rates of at least 1 ft/min, e.g., at least 2 ft/min, at least 3 ft/min, at least 4 ft/min, at least 5 ft/min, at least 10 ft/min, at least 15 ft/min, 20, 25, 30, 35, 40, 45, 50 ft/min. The rate of conveying is related to the beam current, for example, for a ¼ inch thick biomass and 100 mA, the conveyor can move at about 20 ft/min to provide a useful irradiation dosage, at 50 mA the conveyor can move at about 10 ft/min to provide approximately the same irradiation dosage.

After the biomass material has been conveyed through the radiation zone, optional post-treatment processing can be done. The optional post-treatment processing can, for example, be a process described with respect to the pre-irradiation processing. For example, the biomass can be screened, heated, cooled, and/or combined with additives. Uniquely to post-irradiation, quenching of the radicals can occur, for example, quenching of radicals by the addition of fluids or gases (e.g., oxygen, nitrous oxide, ammonia, liquids), using pressure, heat, and/or the addition of radical scavengers. For example, the biomass can be conveyed out of the enclosed conveyor and exposed to a gas (e.g., oxygen) where it is quenched, forming caboxylated groups. In one embodiment the biomass is exposed during irradiation to the reactive gas or fluid. Quenching of biomass that has been irradiated is described in U.S. Pat. No. 8,083,906 to Medoff, the entire disclosure of which is incorporate herein by reference.

If desired, one or more mechanical treatments can be used in addition to irradiation to further reduce the recalcitrance of the biomass material. These processes can be applied before, during and/or after irradiation.

In some cases, the mechanical treatment may include an initial preparation of the feedstock as received, e.g., size reduction of materials, such as by comminution, e.g., cutting, grinding, shearing, pulverizing or chopping. For example, in some cases, loose feedstock (e.g., recycled paper, starchy materials, or switchgrass) is prepared by shearing or shredding. Mechanical treatment may reduce the bulk density of the biomass material, increase the surface area of the biomass material and/or decrease one or more dimensions of the biomass material.

Alternatively, or in addition, the feedstock material can first be physically treated by one or more of the other physical treatment methods, e.g., chemical treatment, radiation, sonication, oxidation, pyrolysis or steam explosion, and then mechanically treated. This sequence can be advantageous since materials treated by one or more of the other treatments, e.g., irradiation or pyrolysis, tend to be more brittle and, therefore, it may be easier to further change the structure of the material by mechanical treatment. For example, a feedstock material can be conveyed through ionizing radiation using a conveyor as described herein and then mechanically treated. Chemical treatment can remove some or all of the lignin (for example chemical pulping) and can partially or completely hydrolyze the material. The methods also can be used with pre-hydrolyzed material. The methods also can be used with material that has not been pre-hydrolyzed. The methods can be used with mixtures of hydrolyzed and non-hydrolyzed materials, for example with about 50% or more non-hydrolyzed material, with about 60% or more non-hydrolyzed material, with about 70% or more non-hydrolyzed material, with about 80% or more non-hydrolyzed material or even with 90% or more non-hydrolyzed material.

In addition to size reduction, which can be performed initially and/or later in processing, mechanical treatment can also be advantageous for "opening up," "stressing," breaking or shattering the biomass materials, making the cellulose of the materials more susceptible to chain scission and/or disruption of crystalline structure during the physical treatment.

Methods of mechanically treating the biomass material include, for example, milling or grinding. Milling may be performed using, for example, a mill, ball mill, colloid mill, conical or cone mill, disk mill, edge mill, Wiley mill, grist mill or other mill. Grinding may be performed using, for example, a cutting/impact type grinder. Some exemplary grinders include stone grinders, pin grinders, coffee grinders, and burr grinders. Grinding or milling may be provided, for example, by a reciprocating pin or other element, as is the case in a pin mill. Other mechanical treatment methods include mechanical ripping, tearing, shearing or chopping, other methods that apply pressure to the fibers, and air attrition milling. Suitable mechanical treatments further include any other technique that continues the disruption of the internal structure of the material that was initiated by the previous processing steps.

Mechanical feed preparation systems can be configured to produce streams with specific characteristics such as, for example, specific maximum sizes, specific length-to-width, or specific surface areas ratios. Physical preparation can increase the rate of reactions, improve the movement of material on a conveyor, improve the irradiation profile of the material, improve the radiation uniformity of the material, or reduce the processing time required by opening up the materials and making them more accessible to processes and/or reagents, such as reagents in a solution.

The bulk density of feedstocks can be controlled (e.g., increased). In some situations, it can be desirable to prepare a low bulk density material, e.g., by densifying the material (e.g., densification can make it easier and less costly to transport to another site) and then reverting the material to a lower bulk density state (e.g., after transport). The material can be densified, for example from less than about 0.2 g/cc to more than about 0.9 g/cc (e.g., less than about 0.3 to more than about 0.5 g/cc, less than about 0.3 to more than about 0.9 g/cc, less than about 0.5 to more than about 0.9 g/cc, less than about 0.3 to more than about 0.8 g/cc, less than about 0.2 to more than about 0.5 g/cc). For example, the material can be densified by the methods and equipment disclosed in U.S. Pat. No. 7,932,065 to Medoff and International Publication No. WO 2008/073186 published Jun. 19, 2008 (which was filed Oct. 26, 2007, was published in English, and which designated the United States), the full disclosures of which are incorporated herein by reference. Densified materials can be processed by any of the methods described herein, or any material processed by any of the methods described herein can be subsequently densified.

In some embodiments, the material to be processed is in the form of a fibrous material that includes fibers provided by shearing a fiber source. For example, the shearing can be performed with a rotary knife cutter.

For example, a fiber source, e.g., that is recalcitrant or that has had its recalcitrance level reduced, can be sheared, e.g., in a rotary knife cutter, to provide a first fibrous material. The first fibrous material is passed through a first screen, e.g., having an average opening size of 1.59 mm or less (1/16 inch, 0.0625 inch), provide a second fibrous material. If desired, the fiber source can be cut prior to the shearing, e.g., with a shredder. For example, when a paper is used as the fiber source, the paper can be first cut into strips that are, e.g., ¼- to ½-inch wide, using a shredder, e.g., a counter-rotating screw shredder, such as those manufactured by Munson (Utica, N.Y.). As an alternative to shredding, the paper can be reduced in size by cutting to a desired size using a guillotine cutter. For example, the guillotine cutter can be used to cut the paper into sheets that are, e.g., 10 inches wide by 12 inches long.

In some embodiments, the shearing of the fiber source and the passing of the resulting first fibrous material through a first screen are performed concurrently. The shearing and the passing can also be performed in a batch-type process.

For example, a rotary knife cutter can be used to concurrently shear the fiber source and screen the first fibrous material. A rotary knife cutter includes a hopper that can be loaded with a shredded fiber source prepared by shredding a fiber source. The shredded fiber source.

In some implementations, the feedstock is physically treated prior to saccharification and/or fermentation. Physical treatment processes can include one or more of any of those described herein, such as mechanical treatment, chemical treatment, irradiation, sonication, oxidation, pyrolysis or steam explosion. Treatment methods can be used in combinations of two, three, four, or even all of these technologies (in any order). When more than one treatment method is used, the methods can be applied at the same time or at different times. Other processes that change a molecular structure of a biomass feedstock may also be used, alone or in combination with the processes disclosed herein.

Mechanical treatments that may be used, and the characteristics of the mechanically treated biomass materials, are described in further detail in U.S. Pat. App. Pub. 2012/0100577 A1, filed Oct. 18, 2011, published Apr. 26, 2013, the full disclosure of which is hereby incorporated herein by reference.

Treatment of Biomass Material—Particle Bombardment

One or more treatments with energetic particle bombardment can be used to process raw feedstock from a wide variety of different sources to extract useful substances from the feedstock, and to provide partially degraded organic material which functions as input to further processing steps and/or sequences. Particle bombardment can reduce the molecular weight and/or crystallinity of feedstock. In some embodiments, energy deposited in a material that releases an electron from its atomic orbital can be used to treat the materials. The bombardment may be provided by heavy charged particles (such as alpha particles or protons), electrons (produced, for example, in beta decay or electron beam accelerators), or electromagnetic radiation (for example, gamma rays, x rays, or ultraviolet rays). Alternatively, radiation produced by radioactive substances can be used to treat the feedstock. Any combination, in any order, or concurrently of these treatments may be utilized. In another approach, electromagnetic radiation (e.g., produced using electron beam emitters) can be used to treat the feedstock.

Each form of energy ionizes the biomass via particular interactions. Heavy charged particles primarily ionize matter via Coulomb scattering; furthermore, these interactions produce energetic electrons that may further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium.

When particles are utilized, they can be neutral (uncharged), positively charged or negatively charged. When charged, the charged particles can bear a single positive or negative charge, or multiple charges, e.g., one, two, three or even four or more charges. In instances in which chain scission is desired, positively charged particles may be desirable, in part, due to their acidic nature. When particles are utilized, the particles can have the mass of a resting electron, or greater, e.g., 500, 1000, 1500, or 2000 or more times the mass of a resting electron. For example, the particles can have a mass of from about 1 atomic unit to about 150 atomic units, e.g., from about 1 atomic unit to about 50 atomic units, or from about 1 to about 25, e.g., 1, 2, 3, 4, 5, 10, 12 or 15 atomic units. Accelerators used to accelerate the particles can be electrostatic DC, electrodynamic DC, RF linear, magnetic induction linear or continuous wave. For example, cyclotron type accelerators are available from IBA (Ion Beam Accelerators, Louvain-la-Neuve, Belgium), such as the Rhodotron™ system, while DC type accelerators are available from RDI, now IBA Industrial, such as the Dynamitron™. Ions and ion accelerators are discussed in Introductory Nuclear Physics, Kenneth S. Krane, John Wiley & Sons, Inc. (1988), Krsto Prelec, FIZIKA B 6 (1997) 4, 177-206; Chu, William T., "Overview of Light-Ion Beam Therapy", Columbus-Ohio, ICRU-IAEA Meeting, 18-20 Mar. 2006; Iwata, Y. et al., "Alternating-Phase-Focused IH-DTL for Heavy-Ion Medical Accelerators", Proceedings of EPAC 2006, Edinburgh, Scotland; and Leitner, C. M. et al., "Status of the Superconducting ECR Ion Source Venus", Proceedings of EPAC 2000, Vienna, Austria.

The doses applied depend on the desired effect and the particular feedstock. For example, high doses can break chemical bonds within feedstock components and low doses can increase chemical bonding (e.g., cross-linking) within feedstock components.

In some instances when chain scission is desirable and/or polymer chain functionalization is desirable, particles heavier than electrons, such as protons, helium nuclei, argon ions, silicon ions, neon ions, carbon ions, phosphorus ions, oxygen ions or nitrogen ions can be utilized. When ring-opening chain scission is desired, positively charged particles can be utilized for their Lewis acid properties for enhanced ring-opening chain scission. For example, when oxygen-containing functional groups are desired, treatment in the presence of oxygen or even treatment with oxygen ions can be performed. For example, when nitrogen-containing functional groups are desirable, treatment in the presence of nitrogen or even treatment with nitrogen ions can be performed.

Other Forms of Energy

Electrons interact via Coulomb scattering and bremsstrahlung radiation produced by changes in the velocity of electrons. Electrons may be produced by radioactive nuclei that undergo beta decay, such as isotopes of iodine, cesium, technetium, and iridium. Alternatively, an electron gun can be used as an electron source via thermionic emission.

Electromagnetic radiation interacts via three processes: photoelectric absorption, Compton scattering, and pair production. The dominating interaction is determined by the energy of the incident radiation and the atomic number of the material. The summation of interactions contributing to the absorbed radiation in cellulosic material can be expressed by the mass absorption coefficient.

Electromagnetic radiation is subclassified as gamma rays, x rays, ultraviolet rays, infrared rays, microwaves, or radiowaves, depending on the wavelength.

For example, gamma radiation can be employed to treat the materials. Gamma radiation has the advantage of a significant penetration depth into a variety of material in the sample. Sources of gamma rays include radioactive nuclei, such as isotopes of cobalt, calcium, technetium, chromium, gallium, indium, iodine, iron, krypton, samarium, selenium, sodium, thalium, and xenon.

Sources of x rays include electron beam collision with metal targets, such as tungsten or molybdenum or alloys, or compact light sources, such as those produced commercially by Lyncean.

Sources for ultraviolet radiation include deuterium or cadmium lamps.

Sources for infrared radiation include sapphire, zinc, or selenide window ceramic lamps.

Sources for microwaves include klystrons, Slevin type RF sources, or atom beam sources that employ hydrogen, oxygen, or nitrogen gases.

Various other devices may be used in the methods disclosed herein, including field ionization sources, electrostatic ion separators, field ionization generators, thermionic emission sources, microwave discharge ion sources, recirculating or static accelerators, dynamic linear accelerators, van de Graaff accelerators, and folded tandem accelerators. Such devices are disclosed, for example, in U.S. Pat. No. 7,931,784 B2, the complete disclosure of which is incorporated herein by reference.

Treatment of Biomass Material—Electron Bombardment

The feedstock may be treated with electron bombardment to modify its structure and thereby reduce its recalcitrance. Such treatment may, for example, reduce the average molecular weight of the feedstock, change the crystalline structure of the feedstock, and/or increase the surface area and/or porosity of the feedstock.

Electron bombardment via an electron beam is generally preferred, because it provides very high throughput and because the use of a relatively low voltage/high power electron beam device eliminates the need for expensive concrete vault shielding, as such devices are "self-shielded" and provide a safe, efficient process. While the "self-shielded" devices do include shielding (e.g., metal plate shielding), they do not require the construction of a concrete vault, greatly reducing capital expenditure and often allowing an existing manufacturing facility to be used without expensive modification. Electron beam accelerators are available, for example, from IBA (Ion Beam Applications, Louvain-la-Neuve, Belgium), Titan Corporation (San Diego, Calif., USA), and NHV Corporation (Nippon High Voltage, Japan).

Electron bombardment may be performed using an electron beam device that has a nominal energy of less than 10 MeV, e.g., less than 7 MeV, less than 5 MeV, or less than 2 MeV, e.g., from about 0.5 to 1.5 MeV, from about 0.8 to 1.8 MeV, from about 0.7 to 1 MeV, or from about 1 to 3 MeV. In some implementations the nominal energy is about 500 to 800 keV.

The electron beam may have a relatively high total beam power (the combined beam power of all accelerating heads, or, if multiple accelerators are used, of all accelerators and all heads), e.g., at least 25 kW, e.g., at least 30, 40, 50, 60, 65, 70, 80, 100, 125, or 150 kW. In some cases, the power is even as high as 500 kW, 750 kW, or even 1000 kW or more. In some cases the electron beam has a beam power of 1200 kW or more.

This high total beam power is usually achieved by utilizing multiple accelerating heads. For example, the electron beam device may include two, four, or more accelerating heads. The use of multiple heads, each of which has a relatively low beam power, prevents excessive temperature rise in the material, thereby preventing burning of the material, and also increases the uniformity of the dose through the thickness of the layer of material.

In some implementations, it is desirable to cool the material during electron bombardment. For example, the material can be cooled while it is being conveyed, for example by a screw extruder or other conveying equipment.

To reduce the energy required by the recalcitrance-reducing process, it is desirable to treat the material as quickly as possible. In general, it is preferred that treatment be performed at a dose rate of greater than about 0.25 Mrad per second, e.g., greater than about 0.5, 0.75, 1, 1.5, 2, 5, 7, 10, 12, 15, or even greater than about 20 Mrad per second, e.g., about 0.25 to 2 Mrad per second. Higher dose rates generally require higher line speeds, to avoid thermal decomposition of the material. In one implementation, the accelerator is set for 3 MeV, 50 mAmp beam current, and the line speed is 24 feet/minute, for a sample thickness of about 20 mm (e.g., comminuted corn cob material with a bulk density of 0.5 g/cm$^3$).

In some embodiments, electron bombardment is performed until the material receives a total dose of at least 0.5 Mrad, e.g., at least 5, 10, 20, 30 or at least 40 Mrad. In some embodiments, the treatment is performed until the material receives a dose of from about 0.5 Mrad to about 150 Mrad, about 1 Mrad to about 100 Mrad, about 2 Mrad to about 75 Mrad, 10 Mrad to about 50 Mrad, e.g., about 5 Mrad to about 50 Mrad, from about 20 Mrad to about 40 Mrad, about 10 Mrad to about 35 Mrad, or from about 25 Mrad to about 30 Mrad. In some implementations, a total dose of 25 to 35 Mrad is preferred, applied ideally over a couple of seconds, e.g., at 5 Mrad/pass with each pass being applied for about one second. Applying a dose of greater than 7 to 8 Mrad/pass can in some cases cause thermal degradation of the feedstock material.

Using multiple heads as discussed above, the material can be treated in multiple passes, for example, two passes at 10 to 20 Mrad/pass, e.g., 12 to 18 Mrad/pass, separated by a few seconds of cool-down, or three passes of 7 to 12 Mrad/pass, e.g., 9 to 11 Mrad/pass. As discussed above, treating the material with several relatively low doses, rather than one high dose, tends to prevent overheating of the material and also increases dose uniformity through the thickness of the material. In some implementations, the material is stirred or otherwise mixed during or after each pass and then smoothed into a uniform layer again before the next pass, to further enhance treatment uniformity.

In some embodiments, electrons are accelerated to, for example, a speed of greater than 75 percent of the speed of light, e.g., greater than 85, 90, 95, or 99 percent of the speed of light.

In some embodiments, any processing described herein occurs on lignocellulosic material that remains dry as acquired or that has been dried, e.g., using heat and/or reduced pressure. For example, in some embodiments, the cellulosic and/or lignocellulosic material has less than about five percent by weight retained water, measured at 25° C. and at fifty percent relative humidity.

Electron bombardment can be applied while the cellulosic and/or lignocellulosic material is exposed to air, oxygen-enriched air, or even oxygen itself, or blanketed by an inert gas such as nitrogen, argon, or helium. When maximum oxidation is desired, an oxidizing environment is utilized, such as air or oxygen and the distance from the beam source is optimized to maximize reactive gas formation, e.g., ozone and/or oxides of nitrogen.

In some embodiments, two or more electron sources are used, such as two or more ionizing sources. For example, samples can be treated, in any order, with a beam of electrons, followed by gamma radiation and UV light having wavelengths from about 100 nm to about 280 nm. In some embodiments, samples are treated with three ionizing radiation sources, such as a beam of electrons, gamma radiation, and energetic UV light. The biomass is conveyed through the treatment zone where it can be bombarded with electrons. It is generally preferred that the bed of biomass material has a relatively uniform thickness, as previously described, while being treated.

It may be advantageous to repeat the treatment to more thoroughly reduce the recalcitrance of the biomass and/or further modify the biomass. In particular the process parameters can be adjusted after a first (e.g., second, third, fourth or more) pass depending on the recalcitrance of the material. In some embodiments, a conveyor can be used which includes a circular system where the biomass is conveyed multiple times through the various processes described above. In some other embodiments multiple treatment devices (e.g., electron beam generators) are used to treat the biomass multiple (e.g., 2, 3, 4 or more) times. In yet other embodiments, a single electron beam generator may be the source of multiple beams (e.g., 2, 3, 4 or more beams) that can be used for treatment of the biomass.

The effectiveness in changing the molecular/supermolecular structure and/or reducing the recalcitrance of the biomass depends on the electron energy used and the dose applied, while exposure time depends on the power and dose.

In some embodiments, the treatment (with any electron source or a combination of sources) is performed until the material receives a dose of at least about 0.05 Mrad, e.g., at least about 0.1, 0.25, 0.5, 0.75, 1.0, 2.5, 5.0, 7.5, 10.0, 15, 20, 25, 30, 40, 50, 60, 70, 80, 90, 100, 125, 150, 175, or 200 Mrad. In some embodiments, the treatment is performed until the material receives a dose of between 0.1-100 Mrad, 1-200, 5-200, 10-200, 5-150, 5-100, 5-50, 5-40, 10-50, 10-75, 15-50, 20-35 Mrad.

In some embodiments, the treatment is performed at a dose rate of between 5.0 and 1500.0 kilorads/hour, e.g., between 10.0 and 750.0 kilorads/hour or between 50.0 and 350.0 kilorads/hours. In other embodiments the treatment is performed at a dose rate of between 10 and 10000 kilorads/hr, between 100 and 1000 kilorad/hr, or between 500 and 1000 kilorads/hr.

Electron Sources

Electrons interact via Coulomb scattering and bremsstrahlung radiation produced by changes in the velocity of electrons. Electrons may be produced by radioactive nuclei that undergo beta decay, such as isotopes of iodine, cesium, technetium, and iridium. Alternatively, an electron gun can be used as an electron source via thermionic emission and accelerated through an accelerating potential. An electron gun generates electrons, accelerates them through a large potential (e.g., greater than about 500 thousand, greater than about 1 million, greater than about 2 million, greater than about 5 million, greater than about 6 million, greater than about 7 million, greater than about 8 million, greater than about 9 million, or even greater than 10 million volts) and then scans them magnetically in the x-y plane, where the electrons are initially accelerated in the z direction down the tube and extracted through a foil window. Scanning the electron beam is useful for increasing the irradiation surface when irradiating materials, e.g., a biomass, that is conveyed through the scanned beam. Scanning the electron beam also distributes the thermal load homogenously on the window and helps reduce the foil window rupture due to local heating by the electron beam. Window foil rupture is a cause of significant down-time due to subsequent necessary repairs and re-starting the electron gun.

Various other irradiating devices may be used in the methods disclosed herein, including field ionization sources, electrostatic ion separators, field ionization generators, thermionic emission sources, microwave discharge ion sources, recirculating or static accelerators, dynamic linear accelerators, van de Graaff accelerators, and folded tandem accelerators. Such devices are disclosed, for example, in U.S. Pat. No. 7,931,784 to Medoff, the complete disclosure of which is incorporated herein by reference.

A beam of electrons can be used as the radiation source. A beam of electrons has the advantages of high dose rates (e.g., 1, 5, or even 10 Mrad per second), high throughput, less containment, and less confinement equipment. Electron beams can also have high electrical efficiency (e.g., 80%), allowing for lower energy usage relative to other radiation methods, which can translate into a lower cost of operation and lower greenhouse gas emissions corresponding to the smaller amount of energy used. Electron beams can be generated, e.g., by electrostatic generators, cascade generators, transformer generators, low energy accelerators with a scanning system, low energy accelerators with a linear cathode, linear accelerators, and pulsed accelerators.

Electrons can also be more efficient at causing changes in the molecular structure of biomass materials, for example, by the mechanism of chain scission. In addition, electrons having energies of 0.5-10 MeV can penetrate low density materials, such as the biomass materials described herein, e.g., materials having a bulk density of less than 0.5 g/cm$^3$, and a depth of 0.3-10 cm. Electrons as an ionizing radiation source can be useful, e.g., for relatively thin piles, layers or beds of materials, e.g., less than about 0.5 inch, e.g., less than about 0.4 inch, 0.3 inch, 0.25 inch, or less than about 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV. Methods of irradiating materials are discussed in U.S. Pat. App. Pub. 2012/0100577 A1, filed Oct. 18, 2011, published Apr. 26, 2012, the entire disclosure of which is herein incorporated by reference.

Electron beam irradiation devices may be procured commercially from Ion Beam Applications (Louvain-la-Neuve, Belgium), the Titan Corporation (San Diego, Calif., USA), and NHV Corporation (Nippon High Voltage, Japan). Typical electron energies can be 0.5 MeV, 1 MeV, 2 MeV, 4.5 MeV, 7.5 MeV, or 10 MeV. Typical electron beam irradiation device power can be 1 KW, 5 KW, 10 KW, 20 KW, 50 KW, 60 KW, 70 KW, 80 KW, 90 KW, 100 KW, 125 KW, 150 KW, 175 KW, 200 KW, 250 KW, 300 KW, 350 KW, 400 KW, 450 KW, 500 KW, 600 KW, 700 KW, 800 KW, 900 KW or even 1000 KW.

Tradeoffs in considering electron beam irradiation device power specifications include cost to operate, capital costs, depreciation, and device footprint. Tradeoffs in considering exposure dose levels of electron beam irradiation would be energy costs and environment, safety, and health (ESH) concerns. Typically, generators are housed in a vault, e.g., of lead or concrete, especially for production from X-rays that are generated in the process. Tradeoffs in considering electron energies include energy costs.

The electron beam irradiation device can produce either a fixed beam or a scanning beam. A scanning beam may be advantageous with large scan sweep length and high scan speeds, as this would effectively replace a large, fixed beam width. Further, available sweep widths of 0.5 m, 1 m, 2 m or more are available. The scanning beam is preferred in most embodiments describe herein because of the larger scan width and reduced possibility of local heating and failure of the windows.

Treatment of Biomass Material—Sonication, Pyrolysis, Oxidation, Steam Explosion

If desired, one or more sonication, pyrolysis, oxidative, or steam explosion processes can be used in addition to or instead of other treatments to further reduce the recalcitrance of the biomass material. These processes can be applied before, during and/or after another treatment or treatments. These processes are described in detail in U.S. Pat. No. 7,932,065 to Medoff, the full disclosure of which is incorporated herein by reference.

Use of Treated Biomass Material

Using the methods described herein, a starting biomass material (e.g., plant biomass, animal biomass, paper, and municipal waste biomass) can be used as feedstock to produce useful intermediates and products such as organic acids, salts of organic acids, anhydrides, esters of organic acids and fuels, e.g., fuels for internal combustion engines or feedstocks for fuel cells. Systems and processes are described herein that can use as feedstock cellulosic and/or lignocellulosic materials that are readily available, but often can be difficult to process, e.g., municipal waste streams and waste paper streams, such as streams that include newspaper, kraft paper, corrugated paper or mixtures of these.

In order to convert the feedstock to a form that can be readily processed, the glucan- or xylan-containing cellulose in the feedstock can be hydrolyzed to low molecular weight carbohydrates, such as sugars, by a saccharifying agent, e.g., an enzyme or acid, a process referred to as saccharification. The low molecular weight carbohydrates can then be used, for example, in an existing manufacturing plant, such as a single cell protein plant, an enzyme manufacturing plant, or a fuel plant, e.g., an ethanol manufacturing facility.

The feedstock can be hydrolyzed using an enzyme, e.g., by combining the materials and the enzyme in a solvent, e.g., in an aqueous solution.

Alternatively, the enzymes can be supplied by organisms that break down biomass, such as the cellulose and/or the lignin portions of the biomass, contain or manufacture various cellulolytic enzymes (cellulases), ligninases or various small molecule biomass-degrading metabolites. These enzymes may be a complex of enzymes that act synergistically to degrade crystalline cellulose or the lignin portions of biomass. Examples of cellulolytic enzymes include: endoglucanases, cellobiohydrolases, and cellobiases (beta-glucosidases).

During saccharification a cellulosic substrate can be initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally, cellobiase cleaves cellobiose to yield glucose. The efficiency (e.g., time to hydrolyze and/or completeness of hydrolysis) of this process depends on the recalcitrance of the cellulosic material.

Intermediates and Products

The processes described herein are preferably used to produce butanol, e.g., isobutanol or n-butanol, and derivatives. However, the processes may be used to produce other products, co-products and intermediates, for example, the products described in U.S. Pat. App. Pub. 2012/0100577 A1, filed Oct. 18, 2011 and published Apr. 26, 2012, the full disclosure of which is incorporated herein by reference.

Using the processes described herein, the biomass material can be converted to one or more products, such as energy, fuels, foods and materials. Specific examples of products include, but are not limited to, hydrogen, sugars (e.g., glucose, xylose, arabinose, mannose, galactose, fructose, disaccharides, oligosaccharides and polysaccharides), alcohols (e.g., monohydric alcohols or dihydric alcohols, such as ethanol, n-propanol, isobutanol, sec-butanol, tert-butanol or n-butanol), hydrated or hydrous alcohols (e.g., containing greater than 10%, 20%, 30% or even greater than 40% water), biodiesel, organic acids, hydrocarbons (e.g., methane, ethane, propane, isobutene, pentane, n-hexane, biodiesel, bio-gasoline and mixtures thereof), co-products (e.g., proteins, such as cellulolytic proteins (enzymes) or single cell proteins), and mixtures of any of these in any combination or relative concentration, and optionally in combination with any additives (e.g., fuel additives). Other examples include carboxylic acids, salts of a carboxylic acid, a mixture of carboxylic acids and salts of carboxylic acids and esters of carboxylic acids (e.g., methyl, ethyl and n-propyl esters), ketones (e.g., acetone), aldehydes (e.g., acetaldehyde), alpha and beta unsaturated acids (e.g., acrylic acid) and olefins (e.g., ethylene). Other alcohols and alcohol derivatives include propanol, propylene glycol, 1,4-butanediol, 1,3-propanediol, sugar alcohols and polyols (e.g., glycol, glycerol, erythritol, threitol, arabitol, xylitol, ribitol, mannitol, sorbitol, galactitol, iditol, inositol, volemitol, isomalt, maltitol, lactitol, maltotriitol, maltotetraitol, and polyglycitol and other polyols), and methyl or ethyl esters of any of these alcohols. Other products include methyl acrylate, methylmethacrylate, lactic acid, citric acid, formic acid, acetic acid, propionic acid, butyric acid, succinic acid, valeric acid, caproic acid, 3-hydroxypropionic acid, palmitic acid, stearic acid, oxalic acid, malonic acid, glutaric acid, oleic acid, linoleic acid, glycolic acid, gamma-hydroxybutyric acid, and mixtures thereof, salts of any of these acids, mixtures of any of the acids and their respective salts.

Any combination of the above products with each other, and/or of the above products with other products, which other products may be made by the processes described herein or otherwise, may be packaged together and sold as products. The products may be combined, e.g., mixed, blended or co-dissolved, or may simply be packaged or sold together.

Any of the products or combinations of products described herein may be sanitized or sterilized prior to selling the products, e.g., after purification or isolation or even after packaging, to neutralize one or more potentially undesirable contaminants that could be present in the product(s). Such sanitation can be done with electron bombardment, for example, be at a dosage of less than about 20 Mrad, e.g., from about 0.1 to 15 Mrad, from about 0.5 to 7 Mrad, or from about 1 to 3 Mrad.

The processes described herein can produce various by-product streams useful for generating steam and electricity to be used in other parts of the plant (co-generation) or sold on the open market. For example, steam generated from burning by-product streams can be used in a distillation process. As another example, electricity generated from burning by-product streams can be used to power electron beam generators used in pretreatment.

The by-products used to generate steam and electricity are derived from a number of sources throughout the process. For example, anaerobic digestion of wastewater can produce a biogas high in methane and a small amount of waste biomass (sludge). As another example, post-saccharification and/or post-distillate solids (e.g., unconverted lignin, cellulose, and hemicellulose remaining from the pretreatment and primary processes) can be used, e.g., burned, as a fuel.

Many of the products obtained, such as ethanol or n-butanol, can be utilized as a fuel for powering cars, trucks, tractors, ships or trains, e.g., as an internal combustion fuel or as a fuel cell feedstock. Many of the products obtained can also be utilized to power aircraft, such as planes, e.g., having jet engines or helicopters. In addition, the products described herein can be utilized for electrical power generation, e.g., in a conventional steam generating plant or in a fuel cell plant.

Other intermediates and products, including food and pharmaceutical products, are described in U.S. Pat. App. Pub. 2010/0124583 A1, published May 20, 2010, to Medoff, the full disclosure of which is hereby incorporated by reference herein.

Post-Processing

The process for purification of products may include using ion-exchange resins, activated charcoal, filtration, distillation, centrifugation, chromatography, precipitation, crystallization, evaporation, adsorption and combinations thereof. In some cases, the fermentation product is also sterilized, e.g., by heat or irradiation.

Saccharification

To obtain a fructose solution from the reduced-relacitrance feedstock, the treated biomass materials can be saccharified, generally by combining the material and a cellulase enzyme in a fluid medium, e.g., an aqueous solution. In some cases, the material is boiled, steeped, or cooked in hot water prior to saccharification, as described in U.S. Pat. App. Pub. 2012/0100577 A1 by Medoff and Masterman, published on Apr. 26, 2012, the entire contents of which are incorporated herein.

The saccharification process can be partially or completely performed in a tank (e.g., a tank having a volume of at least 4000, 40,000, or 500,000 L) in a manufacturing plant, and/or can be partially or completely performed in transit, e.g., in a rail car, tanker truck, or in a supertanker or the hold of a ship. The time required for complete saccharification will depend on the process conditions and the biomass material and enzyme used. If saccharification is performed in a manufacturing plant under controlled conditions, the cellulose may be substantially entirely converted to sugar, e.g., glucose in about 12-96 hours. If saccharification is performed partially or completely in transit, saccharification may take longer.

It is generally preferred that the tank contents be mixed during saccharification, e.g., using jet mixing as described in International App. No. PCT/US2010/035331, filed May 18, 2010, which was published in English as WO 2010/135380 Nov. 25, 2010 and designated the United States, the full disclosure of which is incorporated by reference herein.

In yet a further aspect, the invention features a method that includes converting a low molecular weight sugar to a product by mixing the low molecular weight sugar with a microorganism in a liquid medium, using a jet mixer. The jet mixer can include a jet-flow agitator, jet aeration type mixer, or suction chamber jet mixer.

Various types of mixing devices are described below, and other mixing devices may be used. Suitable mixers have in common that they produce high velocity circulating flow, for example flow in a toroidal or elliptical pattern. Generally, preferred mixers exhibit a high bulk flow rate. Preferred mixers provide this mixing action with relatively low energy consumption. It is also generally preferred that the mixer produce relatively low shear and avoid heating of the liquid medium, as shear and/or heat can deleteriously affect the saccharifying agent (or microorganism, e.g., in the case of fermentation). As will be discussed in detail below, some preferred mixers draw the mixture through an inlet into a mixing element, which may include a rotor or impeller, and then expel the mixture from the mixing element through an outlet nozzle. This circulating action, and the high velocity of the jet exiting the nozzle, assist in dispersing material that is floating on the surface of the liquid or material that has settled to the bottom of the tank, depending on the orientation of the mixing element. Mixing elements can be positioned in different orientations to disperse both floating and settling material, and the orientation of the mixing elements can in some cases be adjustable.

In some preferred mixing systems the velocity $v_o$ of the jet as it meets the ambient fluid is from about 2 to 300 m/s, e.g., about 5 to 150 m/s or about 10 to 100 m/s. The power consumption of the mixing system may be about 20 to 1000 KW, e.g., 30 to 570 KW or 50 to 500 KW, or 150 to 250 KW for a 100,000 L tank. It is generally preferred that the power usage be low for cost-effectiveness.

Jet Mixing

Figure 3:
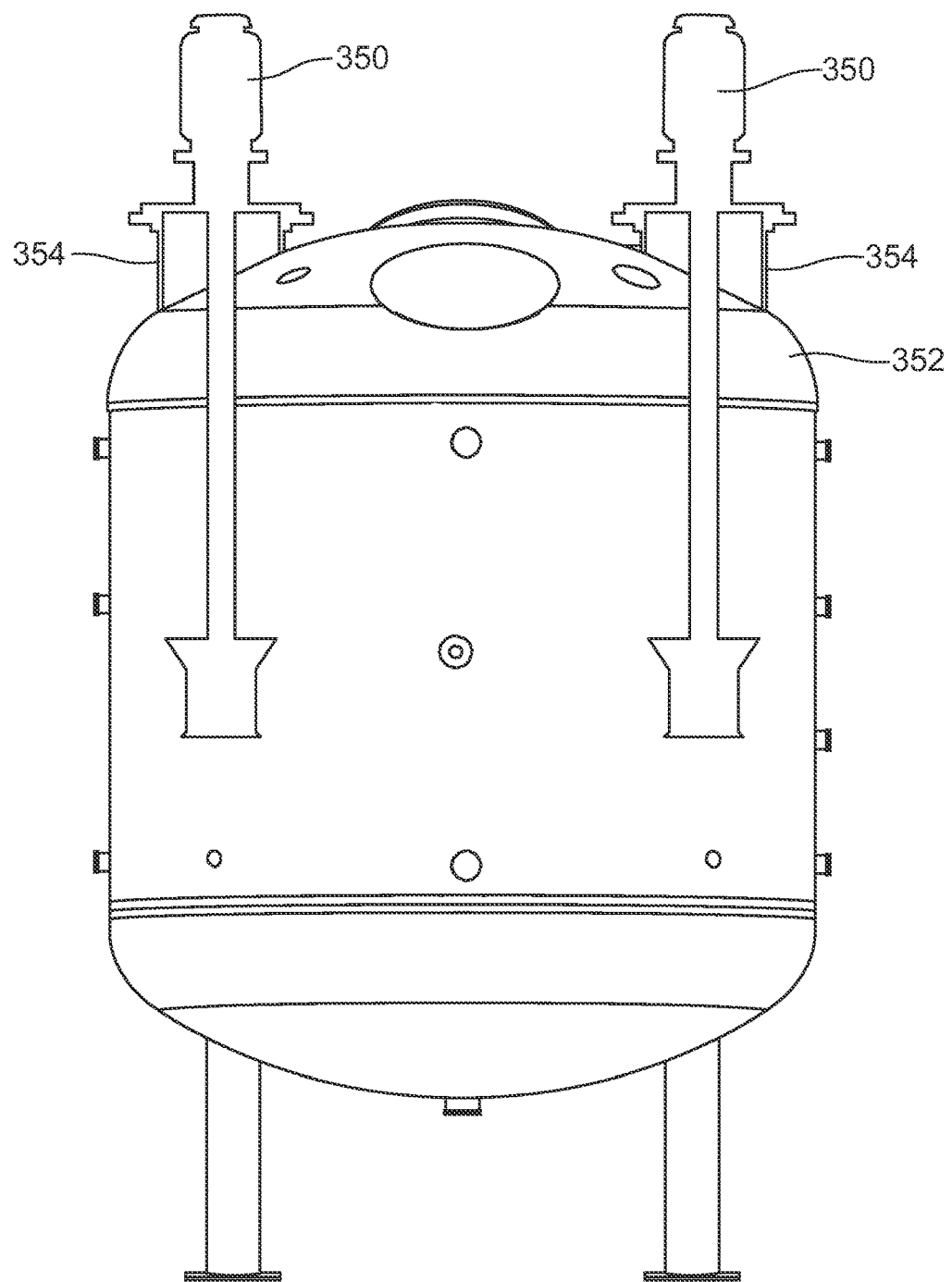
FIG. 3 is a cross-sectional view of a tank having a domed bottom and two jet mixers extending into the tank from above.

Jet mixing involves the discharge of a submerged jet, or a number of submerged jets, of high velocity liquid into a fluid medium, in this case the mixture of biomass feedstock, liquid medium and saccharifying agent. The jet of liquid penetrates the fluid medium, with its energy being dissipated by turbulence and some initial heat. This turbulence is associated with velocity gradients (fluid shear). The surrounding fluid is accelerated and entrained into the jet flow, with this secondary entrained flow increasing as the distance from the jet nozzle increases. The momentum of the secondary flow remains generally constant as the jet expands, as long as the flow does not hit a wall, floor or other obstacle. The longer the flow continues before it hits any obstacle, the more liquid is entrained into the secondary flow, increasing the bulk flow in the tank or vessel. When it encounters an obstacle, the secondary flow will lose momentum, more or less depending on the geometry of the tank, e.g., the angle at which the flow impinges on the obstacle. It is generally desirable to orient the jets and/or design the tank so that hydraulic losses to the tank walls are minimized. For example, it may be desirable for the tank to have an arcuate bottom (e.g., a domed headplate), and for the jet mixers to be oriented relatively close to the sidewalls, as shown in FIG. 3. The tank bottom (lower head plate) may have any desired domed configuration, or may have an elliptical or conical geometry.

Jet mixing differs from most types of liquid/liquid and liquid/solid mixing in that the driving force is hydraulic rather than mechanical. Instead of shearing fluid and propelling it around the mixing vessel, as a mechanical agitator does, a jet mixer forces fluid through one or more nozzles within the tank, creating high-velocity jets that entrain other fluid. The result is shear (fluid against fluid) and circulation, which mix the tank contents efficiently.

Figure 4:
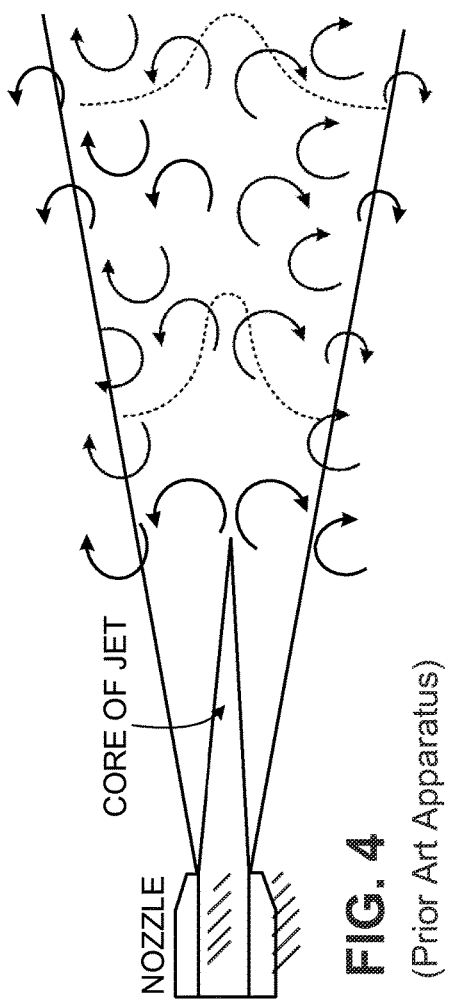
FIGS. 4 and 4A are diagrams illustrating jet flow exiting a nozzle.
Figure 4A:
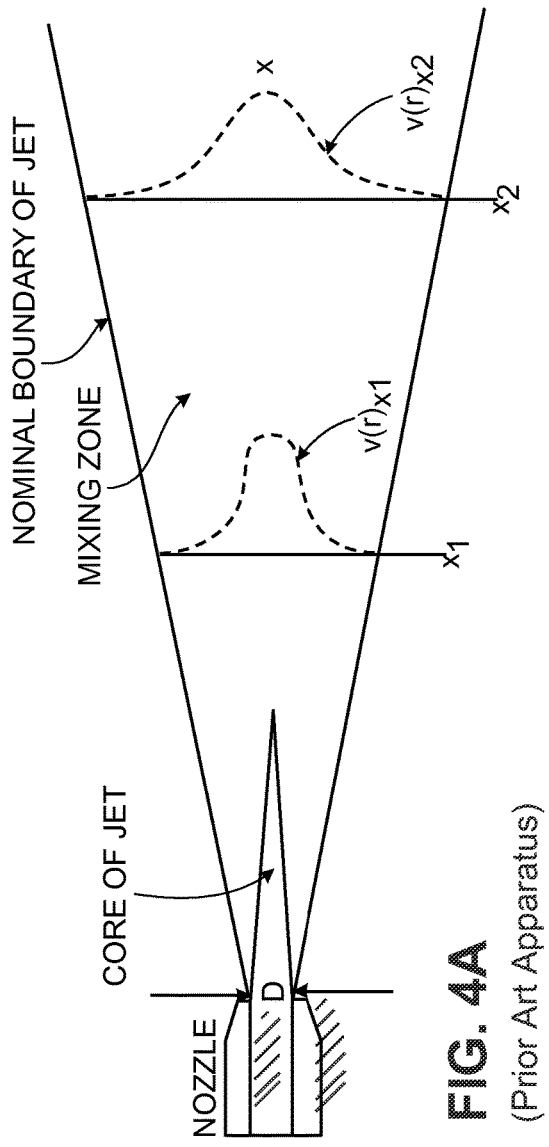

Referring to FIG. 4, the high velocity gradient between the core flow from a submerged jet and the surrounding fluid causes eddies. FIG. 4A illustrates the general characteristics of a submerged jet. As the submerged jet expands into the surrounding ambient environment the velocity profile flattens as the distance (x) from the nozzle increases. Also, the velocity gradient dv/dr changes with r (the distance from the centerline of the jet) at a given distance x, such that eddies are created which define the mixing zone (the conical expansion from the nozzle).

In an experimental study of a submerged jet in air (the results of which are applicable to any fluid, including water), Albertson et al. ("Diffusion of Submerged Jets," Paper 2409, Amer. Soc. of Civil Engineers Transactions, Vol. 115:639-697, 1950, at p. 657) developed dimensionless relationships for v(x)r=0/$v_o$ (centerline velocity), v(r)x/v(x)r=0 (velocity profile at a given x), $Q_x/Q_o$ (flow entrainment), and $E_x/E_o$ (energy change with x):

(1) Centerline velocity, v(x) r=0/$v_o$:

$$\frac{v(r=0)}{v_o} \frac{x}{D_o} = 6.2$$

(2) velocity profile at any x, v(r)x/v(x)r=0:

$$\log\left[\frac{v(r)_x}{v_o} \frac{x}{D}\right] = 0.79 - 33\frac{r^2}{x^2}$$

(3) Flow and energy at any x:

$$\frac{Q_x}{Q_o} = 0.32 \frac{x}{D_o}$$

$$\frac{E_x}{E_o} = 4.1 \frac{D_o}{x}$$

where:
v(r=0)=centerline velocity of submerged jet (m/s),
$v_o$=velocity of jet as it emerges from the nozzle (m/s),
x=distance from nozzle (m),
r=distance from centerline of jet (m),
$D_o$=diameter of nozzle (m),
$Q_x$=flow of fluid across any given plane at distance x from the nozzle (me/s),
$Q_o$=flow of fluid emerging from the nozzle (m3/s),
E=energy flux of fluid across any given plane at distance x from the nozzle (m3/s),
$E_o$=energy flux of fluid emerging from the nozzle (m3/s).

("Water Treatment Unit Processes: Physical and Chemical," David W. Hendricks, CRC Press 2006, p. 411.)

Jet mixing is particularly cost-effective in large-volume (over 1,000 gal) and low-viscosity (under 1,000 cPs) applications. It is also generally advantageous that in most cases the pump or motor of the jet mixer not be submerged, e.g., when a pump is used it is generally located outside the vessel.

One advantage of jet mixing is that the temperature of the ambient fluid (other than directly adjacent the exit of the nozzle, where there may be some localized heating) is increased only slightly if at all. For example, the temperature may be increased by less than 5° C., less than 1° C., or not to any measureable extent.

Jet-Flow Agitators

Figure 5:
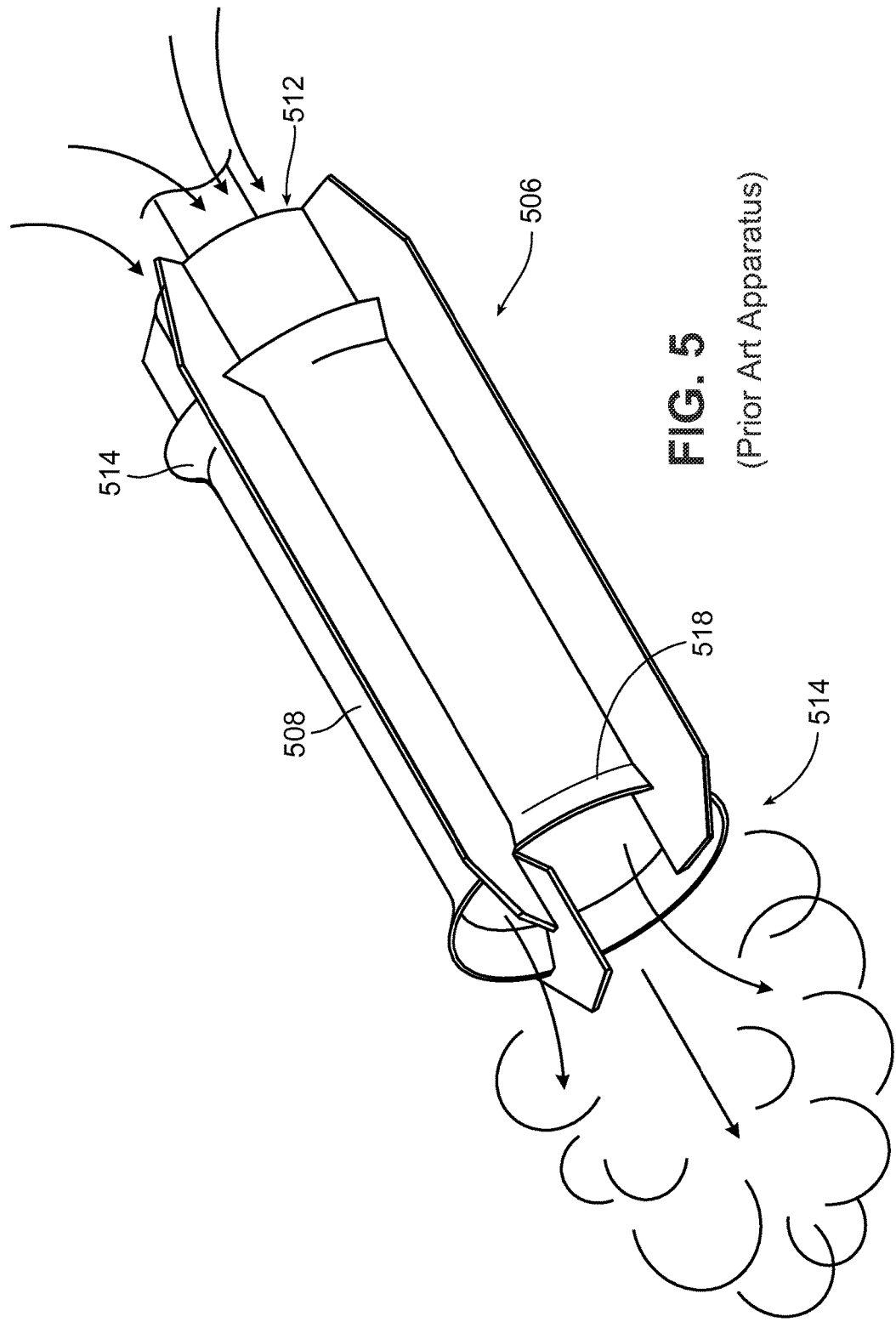
FIG. 5 is a diagrammatic perspective view of a jet-flow agitator according to one embodiment.
Figure 5A:
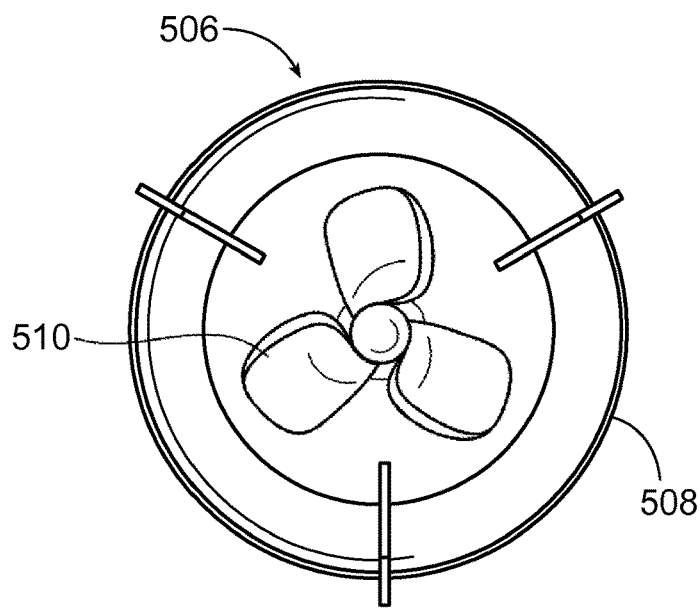
FIG. 5A is an enlarged perspective view of the impeller and jet tube of the jet-flow agitator of FIG. 5.
Figure 5B:
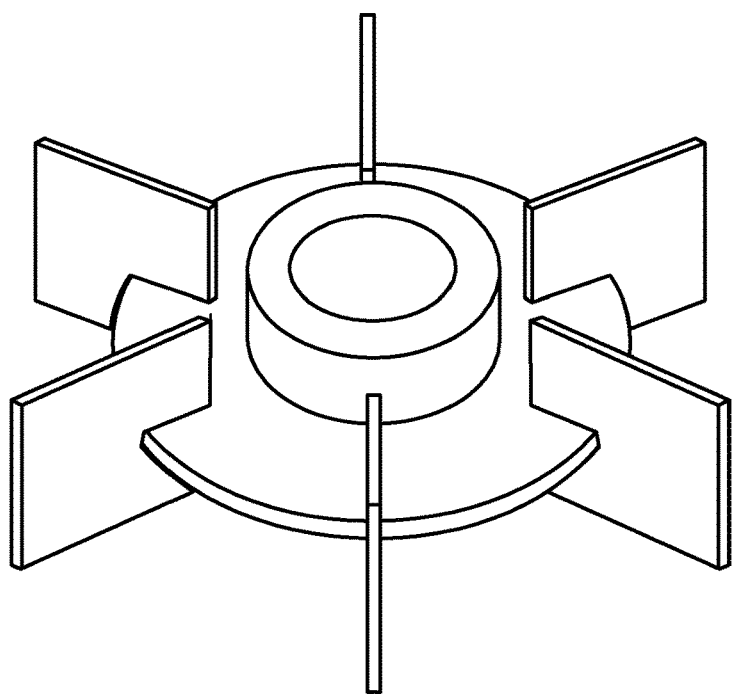
FIG. 5B is an enlarged perspective view of an alternate impeller.

One type of jet-flow agitator is shown in FIGS. 5-5A. This type of mixer is available commercially, e.g., from IKA under the tradename ROTOTRON™. Referring to FIG. 5, the mixer includes a motor, which rotates a drive shaft. A mixing element 506 is mounted at the end of the drive shaft. As shown in FIG. 5A, the mixing element 506 includes a shroud 508 and, within the shroud, an impeller 510. As indicated by the arrows, when the impeller is rotated in its "forward" direction, the impeller 510 draws liquid in through the open upper end 512 of the shroud and forces the liquid out through the open lower end 514. Liquid exiting end 514 is in the form of a high velocity stream or jet. If the direction of rotation of the impeller 510 is reversed, liquid can be drawn in through the lower end 514 and ejected through the upper end 512. This can be used, for example, to suck in solids that are floating near or on the surface of the liquid in a tank or vessel. (It is noted that "upper" and "lower" refer to the orientation of the mixer in FIG. 5; the mixer may be oriented in a tank so that the upper end is below the lower end.)

The shroud 508 includes flared areas 516 and 518 adjacent its ends. These flared areas are believed to contribute to the generally toroidal flow that is observed with this type of mixer. The geometry of the shroud and impeller also concentrate the flow into a high velocity stream using relatively low power consumption.

Preferably, the clearance between the shroud 508 and the impeller 510 is sufficient so as to avoid excessive milling of the material as it passes through the shroud. For example, the clearance may be at least 10 times the average particle size of the solids in the mixture, preferably at least 100 times.

In some implementations, the shaft is configured to allow gas delivery through the shaft. For example, the shaft may include a bore (not shown) through which gas is delivered, and one or more orifices through which gas exits into the mixture. The orifices may be within the shroud 508, to enhance mixing, and/or at other locations along the length of the shaft.

The impeller 510 may have any desired geometry that will draw liquid through the shroud at a high velocity. The impeller is preferably a marine impeller, as shown in FIG. 5A, but may have a different design, for example, a Rushton impeller as shown in FIG. g, or a modified Rushton impeller, e.g., tilted so as to provide some axial flow.

In order to generate the high velocity flow through the shroud, the motor is preferably a high speed, high torque motor, e.g., capable of operating at 500 to 20,000 RPM, e.g., 3,000 to 10,000 RPM. However, the larger the mixer (e.g., the larger the shroud and/or the larger the motor) the lower the rotational speed can be. Thus, if a large mixer is used, such as a 5 hp, 10 hp, 20 hp, or 30 hp or greater, the motor may be designed to operate at lower rotational speeds, e.g., less than 2000 RPM, less than 1500 RPM, or even 500 RPM or less. For example, a mixer sized to mix a 10,000-20,000 liter tank may operate at speeds of 900 to 1,200 RPM. The torque of the motor is preferably self-adjusting, to maintain a relatively constant impeller speed as the mixing conditions change over time, e.g., due to saccharification of the solids.

Advantageously, the mixer can be oriented at any desired angle or location in the tank, to direct the jet flow in a desired direction. Moreover, as discussed above, depending on the direction of rotation of the impeller the mixer can be used to draw fluid from either end of the shroud.

In some implementations, two or more jet mixers are positioned in the vessel, with one or more being configured to jet fluid upward ("up pump") and one or more being configured to jet fluid downward ("down pump"). In some cases, an up pumping mixer will be positioned adjacent a down pumping mixer, to enhance the turbulent flow created by the mixers. If desired, one or more mixers may be switched between upward flow and downward flow during processing. It may be advantageous to switch all or most of the mixers to up pumping mode during initial dispersion of the feedstock in the liquid medium, particularly if the feedstock is dumped or blown onto the surface of the liquid, as up pumping creates significant turbulence at the surface. Up pumping can also be used during fermentation to help remove $CO_2$ from the liquid by causing the gas to bubble to the surface where it can be vented.

The addition of surfactants can enhance the rate of saccharification. Examples of surfactants include non-ionic surfactants, such as a Tween® 20 or Tween® 80 polyethylene glycol surfactants, ionic surfactants, or amphoteric surfactants.

It is generally preferred that the concentration of the sugar solution resulting from saccharification be relatively high, e.g., greater than 40%, or greater than 50, 60, 70, 80, 90 or even greater than 95% by weight. Water may be removed, e.g., by evaporation, to increase the concentration of the sugar solution. This reduces the volume to be shipped, and also inhibits microbial growth in the solution.

Alternatively, sugar solutions of lower concentrations may be used, in which case it may be desirable to add an antimicrobial additive, e.g., a broad spectrum antibiotic, in a low concentration, e.g., 50 to 150 ppm. Other suitable antibiotics include amphotericin B, ampicillin, chloramphenicol, ciprofloxacin, gentamicin, hygromycin B, kanamycin, neomycin, penicillin, puromycin, streptomycin. Antibiotics will inhibit growth of microorganisms during transport and storage, and can be used at appropriate concentrations, e.g., between 15 and 1000 ppm by weight, e.g., between 25 and 500 ppm, or between 50 and 150 ppm. If desired, an antibiotic can be included even if the sugar concentration is relatively high. Alternatively, other additives with anti-microbial of preservative properties may be used. Preferably the antimicrobial additive(s) are food-grade.

A relatively high concentration solution can be obtained by limiting the amount of water added to the biomass material with the enzyme. The concentration can be controlled, e.g., by controlling how much saccharification takes place. For example, concentration can be increased by adding more biomass material to the solution. In order to keep the sugar that is being produced in the solution, a surfactant can be added, e.g., one of those discussed above. Solubility can also be increased by increasing the temperature of the solution. For example, the solution can be maintained at a temperature of 40-50° C., 60-80° C., or even higher.

By adding glucose isomerase to the contents of the tank, a high concentration of fructose can be obtained without saccharification being inhibited by the sugars in the tank. Glucose isomerase can be added in any amount. For example, the concentration may be below about 500 U/g of cellulose (lower than or equal to 100 U/g cellulose, lower than or equal to 50 U/g cellulose, lower than or equal to 10 U/g cellulose, lower than or equal to 5 U/g cellulose). The concentration is at least about 0.1 U/g cellulose (at least about 0.5 U/g cellulose, at least about 1 U/g cellulose, at least about 2 U/g cellulose, at least about 3 U/g cellulose).

The addition of glucose isomerase increases the amount of sugars produced by at least 5% (at least 10%, at least to 15%, at least 20%).

The concentration of sugars in the solution can also be enhanced by limiting the amount of water added to the feedstock with the enzyme, and/or the concentration can be increased by adding more feedstock to the solution during saccharification. In order to keep the sugar that is being produced in the solution, a surfactant can be added, e.g., one of those discussed above. Solubility can also be increased by increasing the temperature of the solution. For example, the solution can be maintained at a temperature of 40-50° C., 60-80° C., or even higher.

Saccharifying Agents

Suitable cellulolytic enzymes include cellulases. Cellulases can be obtained, for example, from species in the genera *Bacillus, Coprinus, Myceliophthora, Cephalosporium, Scytalidium, Penicillium, Aspergillus, Pseudomonas, Humicola, Fusarium, Thielavia, Acremonium, Chrysosporium* and *Trichoderma*, especially those produced by a strain selected from the species *Aspergillus* (see, e.g., EP Pub. No. 0 458 162), *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp. (including, but not limited to, *A. persicinum, A. acremonium, A. brachypenium, A. dichromosporum, A. obclavatum, A. pinkertoniae, A. roseogriseum, A. incoloratum*, and *A. furatum*). Preferred strains include *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Chrysosporium*, preferably a strain of *Chrysosporium lucknowense*. Additional strains that can be used include, but are not limited to, *Trichoderma* (particularly *T. viride, T. reesei*, and *T. koningii*), alkalophilic *Bacillus* (see, for example, U.S. Pat. No. 3,844,890 and EP Pub. No. 0 458 162), and *Streptomyces* (see, e.g., EP Pub. No. 0 458 162).

Many microorganisms that can be used to saccharify biomass material and produce sugars can also be used to ferment and convert those sugars to useful products.

Sugars

In the processes described herein, for example after saccharification, sugars (e.g., glucose and xylose) can be isolated. For example sugars can be isolated by precipitation, crystallization, chromatography (e.g., simulated moving bed chromatography, high pressure chromatography), centrifugation, extraction, any other isolation method known in the art, and combinations thereof.

Hydrogenation and Other Chemical Transformations

The processes described herein can include hydrogenation. For example glucose and xylose can be hydrogenated to sorbitol and xylitol respectively. Hydrogenation can be accomplished by use of a catalyst (e.g., Pt/gamma-$Al_2O_3$, Ru/C, Raney Nickel, or other catalysts know in the art) in combination with $H_2$ under high pressure (e.g., 10 to 12000 psi). Other types of chemical transformation of the products from the processes described herein can be used, for example, production of organic sugar derived products such (e.g., furfural and furfural-derived products). Chemical transformations of sugar derived products are described in U.S. application Ser. No. 13/934,704 filed Jul. 3, 2013, the disclosure of which is incorporated herein by reference in its entirety.

Fermentation

Preferably, *Clostridium* spp. are used to convert sugars (e.g., fructose) to butanol. The optimum pH for fermentations is about pH 4 to 7. For example, the optimum pH for yeast is from about pH 4 to 5, while the optimum pH for *Zymomonas* is from about pH 5 to 6. Typical fermentation times are about 24 to 168 hours (e.g., 24 to 96 hrs) with temperatures in the range of 20° C. to 40° C. (e.g., 26° C. to 40° C.), however thermophilic microorganisms prefer higher temperatures.

In some embodiments, e.g., when anaerobic organisms are used, at least a portion of the fermentation is conducted in the absence of oxygen, e.g., under a blanket of an inert gas such as $N_2$, Ar, He, $CO_2$ or mixtures thereof. Additionally, the mixture may have a constant purge of an inert gas flowing through the tank during part of or all of the fermentation. In some cases, anaerobic condition, can be achieved or maintained by carbon dioxide production during the fermentation and no additional inert gas is needed.

In some embodiments, all or a portion of the fermentation process can be interrupted before the low molecular weight sugar is completely converted to a product (e.g., ethanol). The intermediate fermentation products include sugar and carbohydrates in high concentrations. The sugars and carbohydrates can be isolated via any means known in the art. These intermediate fermentation products can be used in preparation of food for human or animal consumption. Additionally or alternatively, the intermediate fermentation products can be ground to a fine particle size in a stainless-steel laboratory mill to produce a flour-like substance.

Jet mixing may be used during fermentation, and in some cases saccharification and fermentation are performed in the same tank.

Nutrients for the microorganisms may be added during saccharification and/or fermentation, for example the food-based nutrient packages described in U.S. Pat. App. Pub. 2012/0052536, filed Jul. 15, 2011, the complete disclosure of which is incorporated herein by reference.

"Fermentation" includes the methods and products that are disclosed in U.S. Prov. App. No. 61/579,559, filed Dec. 22, 2012, and U.S. Prov. App. No. 61/579,576, filed Dec. 22, 2012, the contents of both of which are incorporated by reference herein in their entirety.

Mobile fermenters can be utilized, as described in International App. No. PCT/US2007/074028 (which was filed Jul. 20, 2007, was published in English as WO 2008/011598 and designated the United States), the contents of which is incorporated herein in its entirety. Similarly, the saccharification equipment can be mobile. Further, saccharification and/or fermentation may be performed in part or entirely during transit.

Fermentation Agents

Although *Clostridium* is preferred, other microorganisms can be used. For instance, yeast and *Zymomonas* bacteria can be used for fermentation or conversion of sugar(s) to other alcohol(s). Other microorganisms are discussed below. They can be naturally-occurring microorganisms and/or engineered microorganisms. For example, the microorganism can be a bacterium (including, but not limited to, e.g., a cellulolytic bacterium), a fungus, (including, but not limited to, e.g., a yeast), a plant, a protist, e.g., a protozoa or a fungus-like protest (including, but not limited to, e.g., a slime mold), or an algae. When the organisms are compatible, mixtures of organisms can be utilized.

Suitable fermenting microorganisms have the ability to convert carbohydrates, such as glucose, fructose, xylose, arabinose, mannose, galactose, oligosaccharides or polysaccharides into fermentation products. Fermenting microorganisms include strains of the genus *Saccharomyces* spp. (including, but not limited to, *S. cerevisiae* (baker's yeast), *S. distaticus, S. Uvarum*), the genus *Kluyveromyces*, (including, but not limited to, *K. marxianus, K. fragilis*), the genus *Candida* (including, but not limited to, *C. pseudotropicalis*, and *C. brassicae*), *Pichia stipitis* (a relative of *Candida shehatae*), the genus *Clavispora* (including, but not limited to, *C. lusitaniae* and *C. opuntiae*), the genus *Pachysolen* (including, but not limited to, *P. tannophilus*), the genus *Bretannomyces* (including, but not limited to, e.g., *B. clausenii* (Philippidis, G. P., 1996, Cellulose bioconversion technology, in Handbook on Bioethanol: Production and Utilization, Wyman, C. E., ed., Taylor & Francis, Washington, DC, 179-212)). Other suitable microorganisms include, for example, *Zymomonas mobilis, Clostridium* spp. (including, but not limited to, *C. thermocellum* (Philippidis, 1996, supra), *C. saccharobutylacetonicum, C. saccharobutylicum, C. Puniceum, C. beijernckii*, and *C. acetobutylicum*), *Moniliella pollinis, Moniliella megachiliensis, Lactobacillus* spp. *Yarrowia lipolytica, Aureobasidium* sp., *Trichosporonoides* sp., *Trigonopsis variabilis, Trichosporon* sp., *Moniliellaacetoabutans* sp., *Typhula variabilis, Candida magnoliae, Ustilaginomycetes* sp., *Pseudozyma tsukubaensis*, yeast species of genera *Zygosaccharomyces, Debaryomyces, Hansenula* and *Pichia*, and fungi of the dematioid genus *Torula*.

For instance, *Clostridium* spp. can be used to produce ethanol, butanol, butyric acid, acetic acid, and acetone. *Lactobacillus* spp., can be used to produce lactic acid.

Many such microbial strains are publicly available, either commercially or through depositories such as the ATCC (American Type Culture Collection, Manassas, Va., USA), the NRRL (Agricultural Research Service Culture Collection, Peoria, Ill., USA), or the DSMZ (Deutsche Sammlung von Mikroorganismen and Zellkulturen GmbH, Braunschweig, Germany), to name a few.

Commercially available yeasts include, for example, Red Star®/Lesaffre Ethanol Red (available from Red Star/Lesaffre, USA), FALI® (available from Fleischmann's Yeast, a division of Burns Philip Food Inc., USA), SUPERSTART® (available from Alltech, now Lalemand), GERT STRAND® (available from Gert Strand AB, Sweden) and FERMOL® (available from DSM Specialties).

Many microorganisms that can be used to saccharify biomass material and produce sugars can also be used to ferment and convert those sugars to useful products.

Distillation

After fermentation, the resulting fluids can be distilled using, for example, a "beer column" to separate ethanol and other alcohols from the majority of water and residual solids. The vapor exiting the beer column can be, e.g., 35% by weight ethanol and can be fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling compounds.

Other than in the examples herein, or unless otherwise expressly specified, all of the numerical ranges, amounts, values and percentages, such as those for amounts of materials, elemental contents, times and temperatures of reaction, ratios of amounts, and others, in the following portion of the specification and attached claims may be read as if prefaced by the word "about" even though the term "about" may not expressly appear with the value, amount, or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains error necessarily resulting from the standard deviation found in its underlying respective testing measurements. Furthermore, when numerical ranges are set forth herein, these ranges are inclusive of the recited range end points (i.e., end points may be used). When percentages by weight are used herein, the numerical values reported are relative to the total weight.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The terms "one," "a," or "an" as used herein are intended to include "at least one" or "one or more," unless otherwise indicated.

EXAMPLES

Example 1. Materials & Methods

Preparation of Seed Cultures:

*Moniliella* cells stored at −80° C. were used to inoculate propagation medium (20 g/L malt extract, 1 g/L peptone, 20 g/L glucose), and incubated at 30° C. and agitation of 200 rpm for 72 hours. The culture was then transferred to a bioreactor (either 3 L, 20 L, or 400 L) for erythritol production.

Main Culture:

The erythritol production medium consists of 10 g/L yeast extract, 1 g/L phytic acid, 1 g/L potassium nitrate, 100 g/L calcium chloride, 10 mg/L cupric sulfate, 50 mg/L zinc chloride and either 300 g/L glucose (reagent grade from Sigma) or purified saccharified corncob prepared in-house.

The corn cob was treated with 35 Mrad from an electron beam, and saccharified with cellulase prepared in-house. The saccharified corn cob was then purified by cation exchange (Diaion PK228, Mitsubishi Chemical Corporation) and anion exchange (Diaion JA300, Mitsubishi Chemical Corporation).

Example 2. Determination of Culture Conditions

The bioreactor culture consisted of 1.5 L in a 3 L vessel, 10 L in a 20 L vessel, or 250 L in a 400 L vessel. Inoculum for each consisted of 72-hour cultured seed culture, added at 5% of the volume in the bioreactor. Aeration was adjusted to 0.3 to 1 VVM, the agitation was 300-1000 rpm, and the temperature was 35° C. Antifoam 204 was added continuously at a rate of 1.5 ml/L/day.

Twelve different yeast extracts were tested for their effect on erythritol production. The results were: Granulated Fisher (105 g/L erythritol production), Thermo Oxoid (30 g/L), Bacto Tech (94 g/L), Fluka (108 g/L), Thermo Remel (111 g/L), Teknova (108 g/L), Acros (93 g/L), Boston (96 g/L), Sunrise (8 g/L), US Biochem (88 g/L), Sigma (76 g/L), and BD (90-120 g/L). Granulated Fisherm Bacto Tech, Fluka, Thermo Remel, Teknova, Acros, Boston, US Biochem, and BD were carried over for additional testing.

Twelve different antifoam agents were tested. These were: Antifoam A, B, C, O-30, SE-15, Y-30, Silicone Antifoam, Antifoam 204 (all from Sigma Chemical Company, St, Louis, Mo., USA), Antifoam AF (from Fisher), KFO 880, KFO 770, and Foam Blast 779 (from Emerald Performance Materials).

TABLE 1a

Medium Components Tested for Erythritol Production

| Medium component | Range Tested | Working Range* | Optimal Range |
|---|---|---|---|
| Phytic acid (culture period) | with phytic acid | 3-4 days to reach max. prod. | with phytic acid |
| Phytic acid (culture period) | without phytic acid | 10-12 days to reach max. prod. | |
| Phytic acid (amount) | 0.3-9 g/L | 0.3-1.0 g/L | 0.3-1.0 g/L |

TABLE 1a-continued

Medium Components Tested for Erythritol Production

| Medium component | Range Tested | Working Range* | Optimal Range |
|---|---|---|---|
| Sodium phosphate monobasic (culture period) | 2-12 g/L | 2-12 g/L (3-4 days to reach max. prod. | lower yield than phytic acid |
| Calcium chloride (amount) | 10-300 mg/L | 10-150 mg/L | 100 mg/L |
| Glucose (amount) | 150-600 g/L | 200-400 g/L | 300 g/L |
| Cupric sulfate (amount) | 2-250 mg/L | 2-250 mg/L | 10 mg/L |
| Yeast extract (amount) | 5-20 g/L | 9-13 g/L | 10 g/L |
| Yeast extract (brand) | 12 different brands | 9 different brands | Fluka YE |
| Zinc chloride (amount) | 25-100 mg/L | 25-100 mg/L | 50 mg/L |
| Antifoam agent (brand) | 12 different agents | KFO 880; Antifoam 204 | Antifoam 204 |
| Nitrogen source | 5 different sources | Urea; Sodium nitrate; Ammonium nitrate; Ammonium sulfate; Potassium nitrate | Potassium nitrate |
| Potassium nitrate (amount) | 0.5-5 g/L | 0.5-5 g/L | 1 g/L |

*"Working Range" was determined as conditions that produced greater than 80 g/L erythritol from 300 g/L glucose.

TABLE 1b

Culture Conditions Tested for Erythritol Production

| Condition Tested | Range Tested | Working Range* | Optimum Range |
|---|---|---|---|
| Agitation (speed in 3 L bioreactor) | 450-1000 rpm | 600-1000 rpm | 800 rpm |
| Agitation (speed in 20 L bioreactor) | 300-650 rpm | 400-650 rpm | 650 rpm |
| Aeration (VVM) | 0.3-1 VVM | 0.3-1 VVM | 0.6 VVM |
| Culture Temperature | 30-40° C. | 30-37° C. | 35° C. |
| Turbulence (dip tube in 400 L bioreactor) | with/without dip tube | with dip tube | with dip tube |

*"Working Range" was determined as conditions that produced greater than 80 g/L erythritol from 300 g/L glucose.

Example 3. Bioreactor Culture of *Moniliella* in a 3 L Bioreactor

*Moniliella pollinis* (strain CBS 461.67; Centraalbureau voor Schimmelcultures, Utrecht, The Netherlands) was cultured in production medium in the 3 L bioreactor (1.5 L culture volume) with various medium components conditions (Table 1a). Phytic acid shortened culture period to 3 to 4 days, while it took 10 to 12 days for erythritol production without phytic acid (Table 1a). Each component (phytic acid, yeast extract, sodium phosphate monobasic, calcium chloride, glucose, cupric sulfate, zinc chloride, potassium nitrate) was tested for obtaining optimal concentration (Table 1a). Physical conditions including agitation, aeration, temperature were also tested (Table 1b). Typical erythritol production was 80 to 120 g/L of erythritol from 300 g/L of glucose.

The table below shows erythritol production in a 3 L bioreactor culture of *Moniliella* strain CBS 461.67 with optimal concentrations of media components (300 g/L glucose, 10 g/L yeast extract, 1 g/L phytic acid, 1 g/L potassium nitrate).

TABLE 2

Production of Erythritol and Other Products From 300 g/L Glucose

| Day | Glycerol | Erythritol | Ribitol | Ethanol |
|---|---|---|---|---|
| 0 | 0 | 0 | 0 | 0 |
| 1 | 7.13 | 3.66 | 0 | 5.39 |
| 2 | 33.50 | 35.69 | 3.51 | 9.68 |
| 3 | 33.77 | 92.13 | 4.79 | 2.86 |
| 4 | 16.89 | 88.51 | 4.92 | 0.45 |

Example 4. Bioreactor Culture of *Moniliella* in a 20 L Bioreactor

Agitation speed was found to greatly affect erythritol production. Erythritol was produced in a 10 L culture volume in a 20 L bioreactor at three different speeds (300 rpm, 400 rpm, 650 rpm), at 1 VVM and 35° C., in medium composed of yeast extract (10 g/L), KNO$_3$ (1 g/L), phytic acid (1 g/L), CuSO$_4$ (2 mg/L). The 400 rpm and 650 rpm cultures also included three impellers. The 650 rpm culture was aerated at 0.6 VVM, rather than 1 VVM.

The bioreactor culture with 300 rpm of agitation speed resulted in much lower erythritol production than the same culture at 650 rpm. Ethanol production, on the other hand, was decreased by increasing agitation speed.

TABLE 3

Effect of Agitation Speed on Erythritol Production.

| Day | Glycerol | Erythritol | Ribitol | Ethanol | Glucose |
|---|---|---|---|---|---|
| | | 300 rpm | | | |
| 0 | 4.09 | 3.35 | 0 | 2.63 | >50 |
| 1 | 10.80 | 5.95 | 3.06 | 15.15 | >50 |
| 2 | 18.48 | 19.39 | 0 | 24.44 | >50 |
| 3 | 24.24 | 48.09 | 0 | 32.37 | 70.74 |
| 4 | 25.27 | 59.51 | 0 | 25.15 | 0 |
| 5 | 23.36 | 64.09 | 3.60 | 8.48 | 0 |

TABLE 3-continued

Effect of Agitation Speed on Erythritol Production.

| Day | Glycerol | Erythritol | Ribitol | Ethanol | Glucose |
|---|---|---|---|---|---|
| 6 | 21.59 | 63.70 | 3.66 | 2.32 | |
| 7 | 19.35 | 59.69 | 3.65 | 1.50 | |
| 400 rpm | | | | | |
| 0 | 0 | 0 | 0 | 0 | 300 |
| 1.3 | 7.09 | 4.21 | 0 | 21.16 | >150 |
| 3 | 16.07 | 80.01 | 3.41 | 22.43 | 48.70 |
| 4 | 9.56 | 92.08 | 3.88 | 11.04 | 0 |
| 4.3 | 7.16 | 94.70 | 3.94 | 4.57 | 0 |
| 5 | 4.08 | 86.30 | 3.68 | 1.31 | 0 |
| 650 rpm | | | | | |
| 0 | 0 | 0 | 0 | 0 | 300 |
| 2 | 18.01 | 89.13 | 4.13 | 6.57 | 112.57 |
| 3 | 30.72 | 145.67 | 6.86 | 1.61 | 4.31 |
| 4 | 16.02 | 129.69 | 6.59 | 1.39 | 0 |
| 5 | 12.65 | 147.54 | 6.87 | | 0 |

Example 5. Bioreactor Culture of *Moniliella* in a 400 L Bioreactor

It was found that the oxygen transfer rate was a key factor in erythritol production in the 400 L bioreactor. Two dip tubes were used to increase the turbulence, an air sparger was installed in the bottom of the vessel, and the aspect ratio was increased. The results (in g/L) are shown in the table below.

TABLE 4

Production of Erythritol and Other Products in a 400 L Bioreactor

| Day | Glycerol | Erythritol | Ribitol | Ethanol |
|---|---|---|---|---|
| 0 | 0 | 0 | 0 | 0 |
| 1 | 6.1 | 9.2 | 1.5 | 15.3 |
| 2 | 10.0 | 60.3 | 1.7 | 19.3 |
| 3 | 11.8 | 75.3 | 0 | 27.7 |

Example 6. Purification of Saccharification Product

Corn cob was saccharified and the resulting sugar mixture purified by ion exchange. Cation exchange and anion exchange were used to remove the metal components listed in the table below.

TABLE 5

Metal elements in ppm in solution of saccharified corn cob containing 100 g/L glucose, before and after ion exchange.

| Element | Before ion exchange | After cation exchange | After cation and anion exchange |
|---|---|---|---|
| Mn | 9 | 0 | 0 |
| Zn | 9 | 0 | 0 |
| Si | 71 | 70 | 0 |
| Fe | 14 | 0 | 0 |
| P | 668 | 704 | 0 |
| K | 4951 | 20 | 0 |
| Mg | 418 | 0 | 0 |
| Na | 10099 | 0 | 0 |
| Ca | 342 | 0 | 0 |
| S | 2048 | 2372 | 37 |

The purified saccharified corn cob solution was then used for erythritol production by two different *Moiliella* strains, CBS 461.67 (*Monilliela pollinis*) and CBS 567.85 (*Moliniella megachiliensis*). Flask cultures were used, and the media components included 10 g/L yeast extract, 1 g/L potassium nitrate, 0.3 g/L phytic acid, 2 mg/L of cupric sulfate as well as purified saccharified corncob. Glucose was consumed in 2 days and little xylose was consumed.

TABLE 6

Erythritol production by two different strains from purified saccharified corn cob containing 160 g/glucose and 140 g/L xylose.

| Day | Glycerol | Erythritol | Ribitol | Ethanol | Fructose |
|---|---|---|---|---|---|
| Strain CBS 461.67 | | | | | |
| 0 | 6.85 | 4.54 | 0 | 0.36 | 9.78 |
| 2 | 9.22 | 31.20 | 0 | 22.35 | 0 |
| 3 | 7.30 | 33.46 | 0 | 19.80 | 0 |
| Strain CBS 567.85 | | | | | |
| 0 | 0 | 4.54 | 0 | 0.21 | 10.30 |
| 2 | 9.72 | 29.36 | 0 | 22.52 | 0 |
| 3 | 7.82 | 45.99 | 0 | 19.47 | 0 |

Erythritol production yield was 21% in CBS 461.67 and 28% in CBS 567.85. This yield is comparable to the erythritol production with reagent grade glucose (30 to 40% yield).

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for making erythritol, said method comprising:
   bombarding a lignocellulosic biomass with electrons to reduce the recalcitrance of said lignocellulosic biomass producing a recalcitrance reduced lignocellulosic biomass,
   saccharifying said recalcitrance reduced lignocellulosic biomass to produce a slurry comprising glucose and xylose,
   combining said slurry with a microorganism selected from the group consisting of CBS 461.67 (*Moniliella pollinis*) and CBS 567.85 (*Moniliella megachiliensis*), and
   fermenting said slurry to produce erythritol, while providing aeration from 0.3 to 1.0 VVM and mixing said slurry with a jet mixer,
   wherein the amount of xylose in said slurry in said fermenting step is equal to the amount of xylose in said lignocellulosic biomass prior to said saccharifying step.

2. The method of claim 1, further comprising adjusting the concentration of said glucose in said slurry to at least 5 wt. % after said saccharifying step.

3. The method of claim 1, wherein said saccharifying step is performed with one or more cellulases.

4. The method of claim 1, wherein said lignocellulosic biomass is selected from the group consisting of: wood, particle board, forestry wastes, sawdust, aspen wood, wood chips, grasses, switchgrass, *miscanthus*, cord grass, reed canary grass, grain residues, rice hulls, oat hulls, wheat chaff, barley hulls, agricultural waste, silage, canola straw, wheat straw, barley straw, oat straw, rice straw, jute, hemp, flax, bamboo, sisal, abaca, corn cobs, corn stover, soybean stover, corn fiber, alfalfa, hay, coconut hair, sugar processing residues, bagasse, beet pulp, agave bagasse, manure, sewage, agricultural or industrial waste, and any combination thereof.

5. The method of claim 1, further comprising mechanically treating said lignocellulosic biomass to reduce its bulk density and/or increase its surface area.

6. The method of claim 1, further comprising comminuting said lignocellulosic biomass.

7. The method of claim 6, wherein said comminuting is dry milling.

8. The method of claim 6, wherein said comminuting is wet milling.

9. The method of claim 1, further comprising culturing said microorganism in a cell growth phase before combining said lignocellulosic biomass with said microorganism.

10. The method of claim 1, wherein said electrons are provided at a dose of at least 5 Mrad.

11. The method of claim 1, wherein said electrons are provided at a dose of between 5 Mrad to 50 Mrad.

12. The method of claim 1, wherein said electrons are provided at a dose of between 20 Mrad to 40 Mrad.

13. The method of claim 1, wherein said electrons are provided at a dose rate of greater than 0.25 Mrad/sec.

14. The method of claim 1, wherein said electrons are provided at a dose rate of between 0.25 to 2 Mrad/sec.

15. The method of claim 1, wherein said electrons are provided at a dose rate of greater than 2 Mrad/sec.

16. The method of claim 1, wherein said jet mixer further comprises an impeller, said impeller rotating at a rate between 400 to 650 revolutions per minute while mixing.

17. The method of claim 1, wherein said jet mixer comprises a shaft, and said method further comprising aerating said slurry through a bore in said shaft.

18. The method of claim 17, wherein said bore provides aeration of 0.6 VVM.

19. The method of claim 1, wherein the yield of erythritol is comparable to a yield of erythritol using reagent grade glucose instead of the slurry.

20. The method of claim 19, wherein the yield of erythritol using reagent grade glucose is 30% to 40%.

21. The method of claim 1, wherein the concentration of sugar in the said slurry is greater than 40 wt %.

22. The method of claim 1, wherein the concentration of glucose in said slurry prior to fermentation is greater than 10 wt %.

23. The method of claim 1, wherein the concentration of glucose in said slurry prior to fermentation is greater than 15 wt %.

24. The method of claim 1, wherein the concentration of glucose in said slurry prior to fermentation is greater than 20 wt %.

* * * * *